US010165939B2

(12) United States Patent
Imamura

(10) Patent No.: US 10,165,939 B2
(45) Date of Patent: Jan. 1, 2019

(54) OPHTHALMOLOGIC APPARATUS AND OPHTHALMOLOGIC APPARATUS CONTROL METHOD

(71) Applicant: CANON KABUSHIKI KAISHA, Tokyo (JP)

(72) Inventor: Hiroshi Imamura, Kyoto (JP)

(73) Assignee: Canon Kabushiki Kaisha, Tokyo (JP)

(*) Notice: Subject to any disclaimer, the term of this patent is extended or adjusted under 35 U.S.C. 154(b) by 125 days.

(21) Appl. No.: 14/842,615

(22) Filed: Sep. 1, 2015

(65) Prior Publication Data
US 2016/0066778 A1    Mar. 10, 2016

(30) Foreign Application Priority Data

Sep. 5, 2014   (JP) ................. 2014-181341

(51) Int. Cl.
*A61B 3/00* (2006.01)
*A61B 3/14* (2006.01)
*A61B 3/10* (2006.01)
*A61B 3/12* (2006.01)

(52) U.S. Cl.
CPC .......... *A61B 3/0025* (2013.01); *A61B 3/0041* (2013.01); *A61B 3/0091* (2013.01); *A61B 3/1015* (2013.01); *A61B 3/1025* (2013.01); *A61B 3/1241* (2013.01); *A61B 3/14* (2013.01); *A61B 3/1233* (2013.01)

(58) Field of Classification Search
CPC ... A61B 3/0025; A61B 3/0041; A61B 3/1015; A61B 3/14
USPC ................................. 351/206, 246
See application file for complete search history.

(56) References Cited

U.S. PATENT DOCUMENTS

| 6,082,859 | A | * | 7/2000 | Okashita | ............. | A61B 3/0091 351/206 |
| 6,773,109 | B2 | * | 8/2004 | Ichikawa | ................. | A61B 3/12 351/206 |
| 6,968,127 | B2 | * | 11/2005 | Nanjyo | .................... | A61B 3/12 351/208 |
| 2007/0237423 | A1 | * | 10/2007 | Tico | ...................... | G06T 3/4038 382/284 |

(Continued)

FOREIGN PATENT DOCUMENTS

| CN | 101926640 A | 12/2010 |
| CN | 102232824 A | 11/2011 |

(Continued)

OTHER PUBLICATIONS

Rafael C. Gonzalez, et al., Digital Image Processing, Technosphere, M., 2005, pp. 879-881, Russia.

*Primary Examiner* — Nicholas R. Pasko
(74) *Attorney, Agent, or Firm* — Canon U.S.A., Inc. IP Division

(57) ABSTRACT

An ophthalmologic apparatus acquires a plurality of images by photographing a plurality of different regions of an eye at different times to generate one image by using the acquired plurality of images. The ophthalmologic apparatus includes a determination unit configured to determine, in the plurality of regions, at least one region that does not include any region actually photographed as the plurality of images, and a control unit configured to control the ophthalmologic apparatus in such a way as to capture an image of the determined region of the eye.

20 Claims, 15 Drawing Sheets

(56) References Cited

U.S. PATENT DOCUMENTS

| | | |
|---|---|---|
| 2009/0244482 A1 | 10/2009 | Elsner |
| 2011/0267580 A1* | 11/2011 | Nakajima .......... G06K 9/00597 |
| | | 351/206 |
| 2011/0292338 A1* | 12/2011 | Iwanaga .................. A61B 3/14 |
| | | 351/206 |
| 2012/0218515 A1 | 8/2012 | Imamura |
| 2012/0249957 A1* | 10/2012 | Shibata ................ A61B 3/0025 |
| | | 351/206 |
| 2014/0078466 A1 | 3/2014 | Sekine |

FOREIGN PATENT DOCUMENTS

| | | |
|---|---|---|
| CN | 102421351 A | 4/2012 |
| CN | 102458227 A | 5/2012 |
| CN | 102670164 A | 9/2012 |
| EP | 2382913 A1 | 11/2011 |
| JP | 2012-213513 A | 11/2012 |
| JP | 2013-169309 A | 9/2013 |
| RU | 2487378 C1 | 7/2013 |
| WO | 2007142960 A2 | 12/2007 |
| WO | 2010/083381 A1 | 7/2010 |
| WO | 2010/128630 A1 | 11/2010 |

* cited by examiner

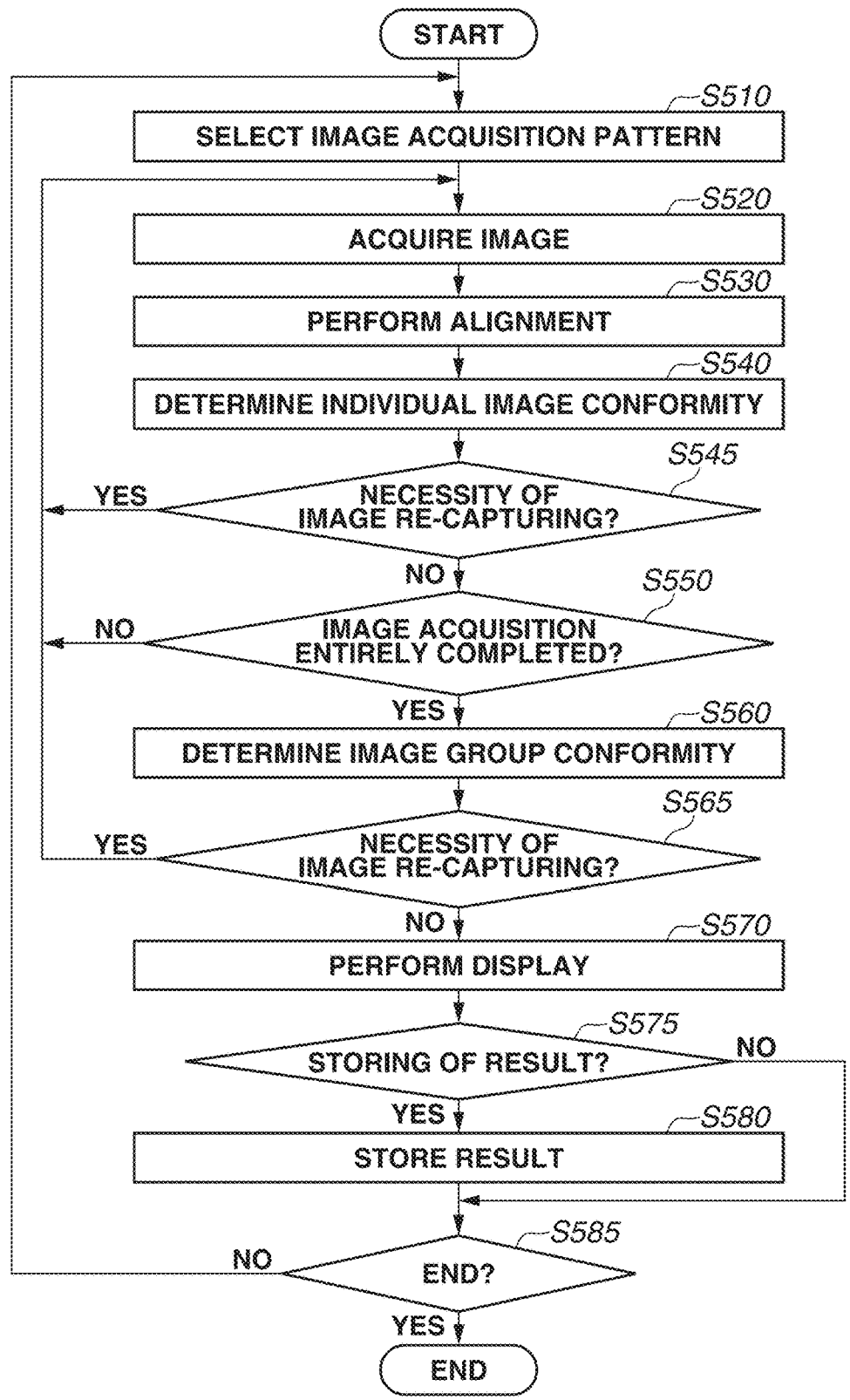

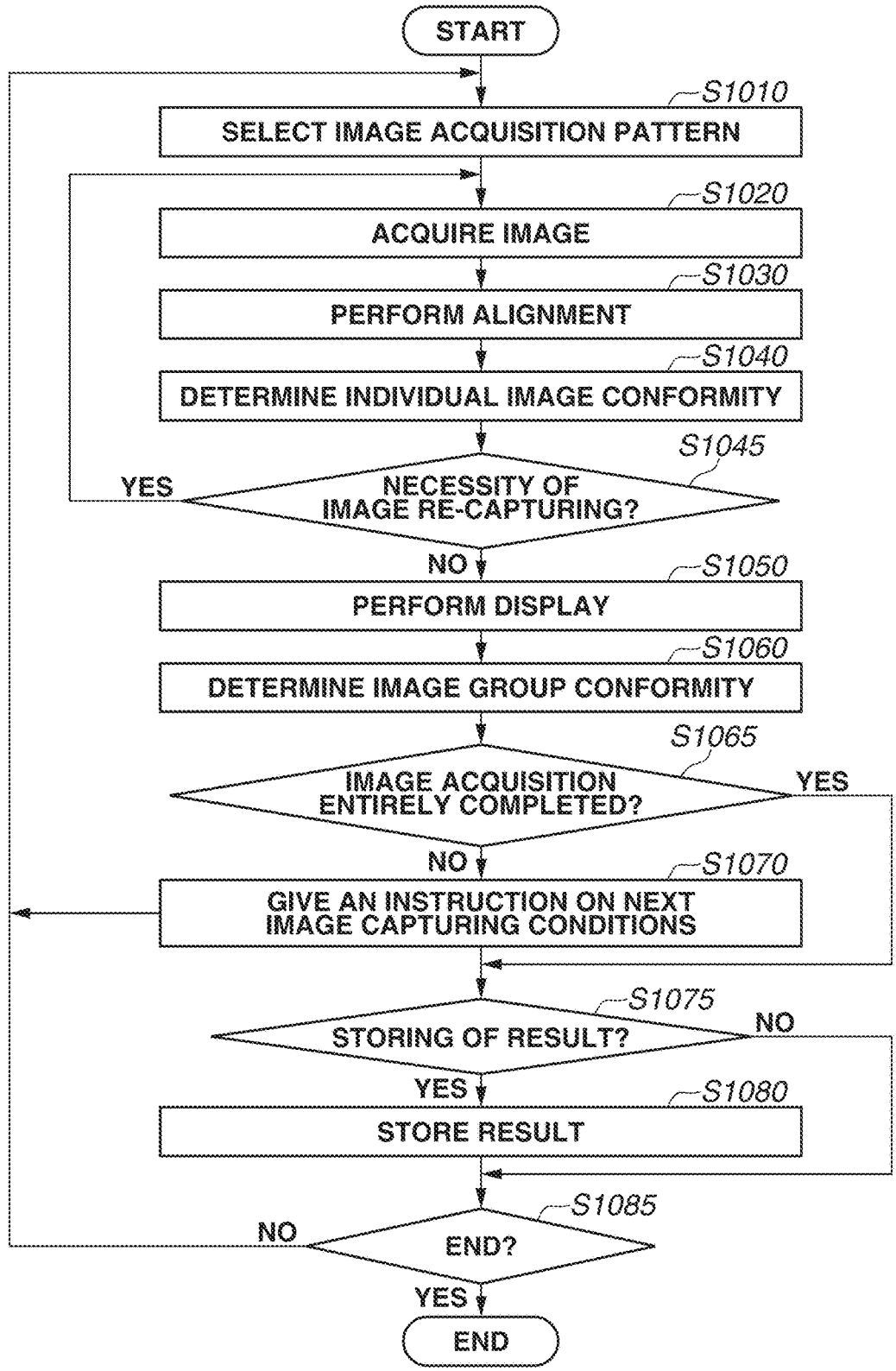

OPHTHALMOLOGIC APPARATUS AND OPHTHALMOLOGIC APPARATUS CONTROL METHOD

BACKGROUND OF THE INVENTION

Field of the Invention

The present invention relates to an ophthalmologic apparatus that can be used in ophthalmologic diagnosis and treatment, and relates to a method for controlling the ophthalmologic apparatus.

Description of the Related Art

Eye examinations have been widely performed for the purpose of early diagnosis and treatment of a lifestyle related disease or a disease having the high possibility of leading the cause of blindness. A scanning laser ophthalmoscope (SLO) is an ophthalmologic apparatus that is operable based on the principle of a confocal laser microscope. The SLO apparatus can perform raster scanning of an eye fundus with laser (i.e., measurement light) and can acquire high-resolution and high-speed plane images based on the intensity of return light. The plane images acquired by the SLO apparatus are hereinafter referred to as SLO images.

A recent SLO apparatus is configured to use measurement light having a larger beam diameter, so that a captured SLO image of a retina is excellent in horizontal resolution. However, if the beam diameter of the measurement light becomes larger, a problem will occur in acquiring an SLO image of a retina. For example, the acquired SLO image will be insufficient in S/N ratio and/or resolution due to aberration of an examinee's eye. To solve the above-mentioned problem, an adaptive optics SLO apparatus can be configured to include a wavefront sensor capable of measuring the aberration of an examinee's eye in real time and a wavefront correcting device capable of correcting the aberration of measurement light or return light occurring in the examinee's eye. The adaptive optics SLO apparatus having the above-mentioned arrangement can acquire SLO images excellent in horizontal resolution (i.e., high magnification images).

The above-mentioned high magnification images can be acquired as a moving image and can be used, for example, to observe blood flow dynamics noninvasively. In this case, it is feasible to extract a retina blood vessel from each frame and measure the moving speed of a blood corpuscle in the capillary. Further, to evaluate the relevancy to the visual function using high magnification images, it is feasible to detect visual cells P and measure the density distribution and/or the arrangement of the visual cells P. FIG. 6B illustrates an example of the high magnification image, in which visual cells P, a low-luminance region Q representing the position of a capillary, and a high-luminance region W representing the position of a white blood cell can be observed.

In this case, in a case where high magnification images are used to observe the visual cells P or measure the distribution of the visual cells P, the focus position is set adjacently to an outer layer of a retina (see B5 in FIG. 6A) to capture a high magnification image as illustrated in FIG. 6B. On the other hand, a retina blood vessel and branched capillaries are extensively distributed in an inner layer of a retina (see B2 to B4 in FIG. 6A). In this case, an imaging target region to be set in capturing an image of an examinee's eye tends to become larger in comparison with the angle of view of the high magnification image. For example, the above-mentioned relationship will be recognized when an imaging target is a visual cell missing region extending in a wide range or a parafovea region (i.e., a favorite site of an initial capillary lesion). In view of the foregoing, as discussed in Japanese Patent Application Laid-Open No. 2012-213513, there is a conventionally known technique capable of displaying an image composite (montaged images) composed of a plurality of high magnification images captured at different photographing positions.

Further, as discussed in Japanese Patent Application Laid-Open No. 2013-169309, there is a conventionally known technique capable of identifying an exceptional frame having a larger influence (e.g., involuntary eye movement) in a high-magnification moving image captured at a specific photographing position and displaying all frames of the high-magnification moving image except for the determined exceptional frames.

SUMMARY OF THE INVENTION

An ophthalmologic apparatus acquires a plurality of images by photographing a plurality of different regions of an eye at different times to generate one image by using the acquired plurality of images. The ophthalmologic apparatus includes a determination unit configured to determine, in the plurality of regions, at least one region that does not include any region actually photographed as the plurality of images, and a control unit configured to control the ophthalmologic apparatus in such a way as to capture an image of the determined region of the eye.

Further features of the present invention will become apparent from the following description of exemplary embodiments with reference to the attached drawings.

BRIEF DESCRIPTION OF THE DRAWINGS

FIG. 5 is a flowchart illustrating processing that can be performed by an ophthalmologic apparatus according to an exemplary embodiment of the present invention.

FIG. 10 is a flowchart illustrating processing that can be performed by the ophthalmologic apparatus according to the third exemplary embodiment of the present invention.

DESCRIPTION OF THE EMBODIMENTS

Figure 1:
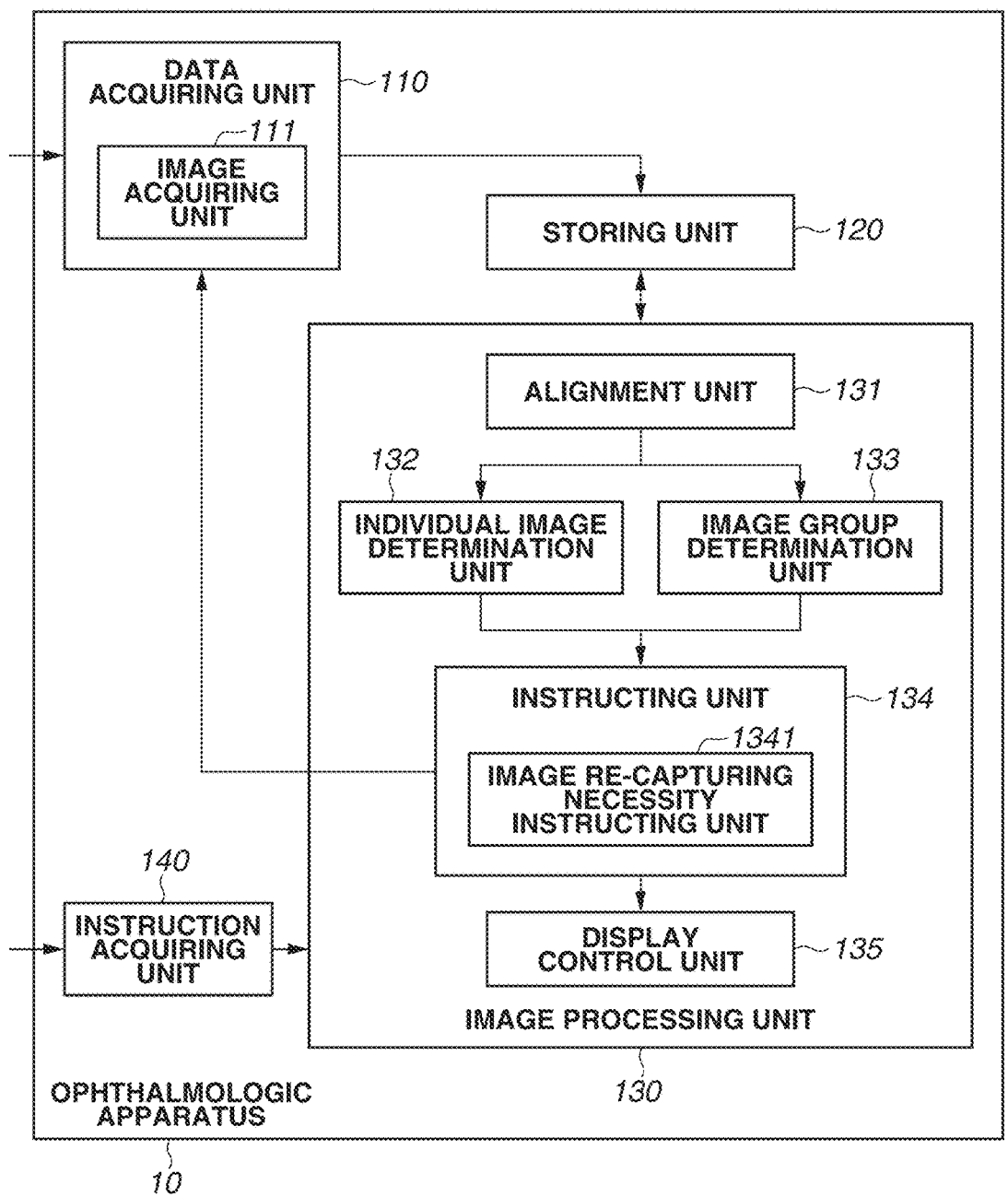
FIG. 1 is a block diagram illustrating a functional configuration of an ophthalmologic apparatus according to a first exemplary embodiment of the present invention.

First, it is now assumed that an ophthalmologic apparatus acquires representative images from among a plurality of high-magnification moving images captured at different photographing positions and then forms and displays a composite of representative images. In general, the ophthalmologic apparatus generates a wide range image by acquiring representative images from among a plurality of high-magnification moving images and forms a composite of the acquired representative images. In this case, two of the representative images captured at neighboring photographing positions may not be sufficient or adequate in the continuity with respect to photographing positions, luminance characteristics, or image features, when compared with each other. If such a wide range image is used to measure the distribution of a cell group or a tissue, and a lesion thereof (defect of visual cells or capillary aneurysm) extending in a wide range, an unanalyzable region may occur or an analysis target may not be extracted.

The present exemplary embodiment intends to provide an ophthalmologic apparatus capable of performing an image capturing operation based on photographing conditions determined in such a way as to improve the continuity of a plurality of high magnification images captured at different photographing positions of an eye.

Therefore, an ophthalmologic apparatus according to the present exemplary embodiment includes a determination unit (e.g., an instructing unit 134 illustrated in FIG. 1) configured to determine photographing conditions for photographing an eye at different positions based on the characteristic continuity between a plurality of images photographed at different positions of the eye (i.e., an image group). Therefore, it becomes feasible to photograph an eye based on photographing conditions capable of improving the continuity between a plurality of high magnification images photographed at different photographing positions.

In this case, the characteristics of a plurality of images (i.e., an image group) can be, for example, at least one of the relative position of the plurality of images, luminance characteristics, and image features. Further, the photographing conditions can include a photographing position (i.e., scanning position), a photographing angle of view (i.e., scanning range), a light emission amount of a light source, gain of a light detector, and a frame rate. Further, each of the images constituting the image group is a representative image acquired from moving images, which can be a sheet of image selected from the moving images. Alternatively, it is feasible to select a plurality of sheets of images that are excellent in noise and artifact characteristics beforehand and then superimpose the selected images to obtain a composite superimposing image.

Further, it is desired that the ophthalmologic apparatus according to the present exemplary embodiment includes a determination unit configured to determine a value indicating continuity, because it is feasible to determine the photographing conditions so that a determined value can satisfy a predetermined condition. For example, the determined value satisfies the predetermined condition when the determined value exceeds a threshold value or when the determined value is maximized. For example, in a case where the determination of the continuity is based on luminance characteristics, it is desired to determine the photographing conditions in such a manner that the difference in luminance value among the acquired images becomes equal to or less than a threshold value. Further, it is desired to use an image composite, which is composed of a plurality of subimages patched together, in determining the value indicating the continuity. For example, the value indicating the continuity can be determined based on the number of subimages constituting the image composite, the areas of subimages, or the length of a non-blood vessel region boundary, as described in detail below in the following exemplary embodiment.

Further, it may be unfeasible to obtain a plurality of images suitable for generating a panoramic image if an involuntary eye movement occurs. As discussed in Japanese Patent Application Laid-Open No. 2012-213513, it is conventionally known that the photographing operation is repetitively performed at the same portion until a predetermined correlation between common portions of neighboring photographed images can be recognized. In this case, even when photographed images suitable for generating a panoramic image can be obtained at a partial region of the same portion, the photographing operation will be repetitively performed for the entire region of the same portion. Therefore, as a result, a long time is required to complete the photographing operation because of photographing at unnecessary regions. The photographing position may deviate due to the involuntary eye movement when the photographing operation is performed for one of a plurality of regions of an eye. However, in this case, there is a possibility that the photographing operation for at least one of other regions is already completed successfully. Therefore, an ophthalmologic apparatus according to another exemplary embodiment captures images of insufficient regions after the photographing operation for a plurality of regions has been completed. Therefore, the ophthalmologic apparatus selectively captures an image of a region that has not been actually photographed with reference to a photographed image of at least one of other regions. Therefore, it is unnecessary to capture images of unnecessary regions in a repetitive photographing operation. The entire photographing time can be reduced.

Hereinafter, ophthalmologic apparatuses and control methods thereof according to preferred exemplary embodiments of the present invention will be described in detail below with reference to attached drawings. However, the present invention is not limited to the above-mentioned examples.

[Continuity of a Plurality of Images Photographed at Different Positions in a Relative Position and Luminance Characteristics]

A first exemplary embodiment will be described in detail below. The ophthalmologic apparatus according to the present exemplary embodiment determines the conformity of a plurality of images (i.e., an image group) photographed at different positions, based on the continuity of the image group at least in one of a relative position and luminance characteristics. If the conformity does not satisfy a predetermined level, the ophthalmologic apparatus instructs an operator to capture an image again for each nonconforming image. Thus, an imaging range can be observed under substantially the same conditions.

Figure 6A:
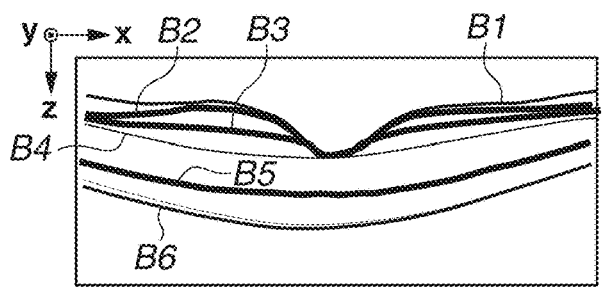
FIGS. 6A, 6B, 6C, 6D, 6E, 6F, 6G, 6H, 6I, and 6J illustrate the contents of image processing according to the first exemplary embodiment of the present invention.
Figure 6B:
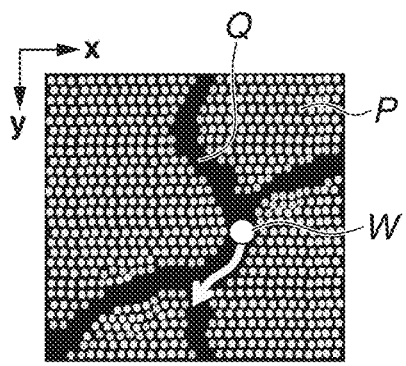
Figure 6C:
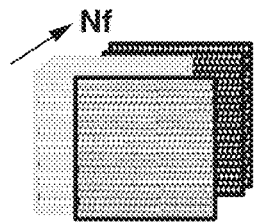
Figure 6D:
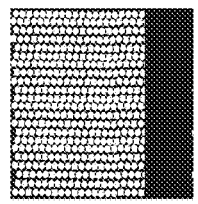
Figure 6E:
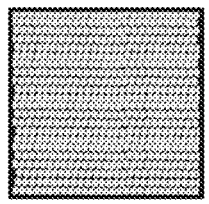
Figure 6F:
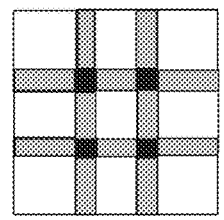
Figure 6G:
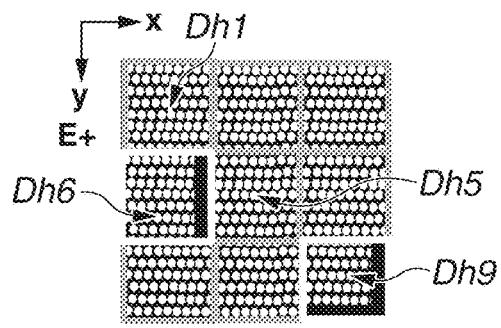

More specifically, it is assumed that an image group is composed of nine sheets of high magnification images, as illustrated in FIG. 6G. The ophthalmologic apparatus determines the image group conformity with reference to the number of images belonging to non-observable regions relative to the number of images that constitute the image group, as described in detail below.

(Entire Configuration)

Figure 2A:
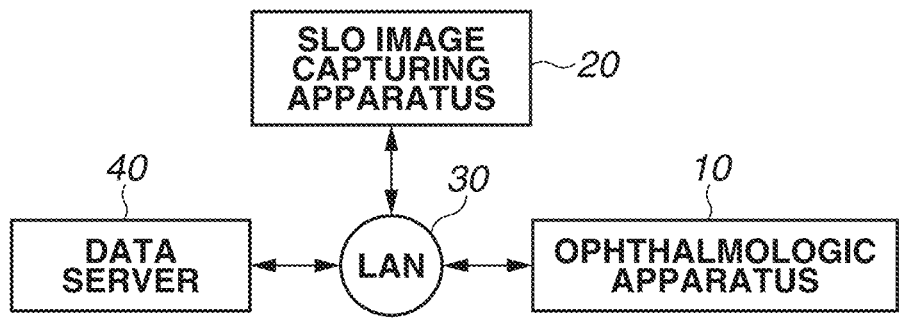
FIGS. 2A, 2B, and 2C are block diagrams each illustrating a configuration of a system including the ophthalmologic apparatus according to an exemplary embodiment of the present invention.

FIG. 2A illustrates a configuration of a system including an ophthalmologic apparatus 10 according to the present exemplary embodiment. As illustrated in FIG. 2A, the ophthalmologic apparatus 10 is connected to an SLO image capturing apparatus 20 and a data server 40 via a local area network (LAN) 30, which can be constituted by an optical fiber, a USB, or IEEE1394. Instead of employing the above-mentioned configuration, the devices can be connected to each other via an external network, such as the internet. Further, the ophthalmologic apparatus 10 can be directly connected to the SLO image capturing apparatus 20.

The SLO image capturing apparatus 20 is capable of acquiring a wide viewing angle image Dl and high magnification images Dh of an eye. The SLO image capturing apparatus 20 can transmit information about the acquired images (i.e., the wide viewing angle image Dl and the high magnification images Dh) together with information about fixation target positions Fl and Fh used in a photographing operation to both the ophthalmologic apparatus 10 and the data server 40. In a case where images of a predetermined magnification are captured at different photographing positions, Dli represents a wide viewing angle image and Dhj represents a high magnification image acquired at each photographing position. More specifically, i and j are variables each indicating a photographing position number (i=1, 2, . . . , and imax, and j=1, 2, . . . , and jmax). Further, in a case where a plurality of high magnification images are acquired at different magnifications, D1$j$, D2$k$, . . . represent captured images sequentially arranged in descending order with respect to the magnitude of magnification. D1$j$ represents the highest magnification image and D2$k$, . . . represent intermediate-magnification images.

Further, the data server 40 can store the wide viewing angle image Dl and the high magnification images Dh of each examinee's eye together with photographing condition data (e.g., the fixation target positions Fl and Fh) used in a photographing operation, in addition to image features of each eye and normal values relating to the distribution of eye image features. The eye image features to be processed in the present invention include visual cells P, a capillary Q, a blood corpuscle W, a retina blood vessel, and a retina layer boundary. The server stores the wide viewing angle images Dl, the high magnification images Dh, and the fixation target positions Fl and Fh used in each photographing operation output from the SLO image capturing apparatus 20 and the eye image features output from the ophthalmologic apparatus 10. Further, in response to a request from the ophthalmologic apparatus 10, the data server 40 can transmit the wide viewing angle images Dl and the high magnification images Dh, in addition to the eye image features and the normal value data relating to the image features to the ophthalmologic apparatus 10.

Next, a functional configuration of the ophthalmologic apparatus 10 according to the present exemplary embodiment will be described in detail below with reference to FIG. 1. FIG. 1 is a block diagram illustrating the functional configuration of the ophthalmologic apparatus 10. The ophthalmologic apparatus 10 includes a data acquiring unit 110, a storing unit 120, an image processing unit 130, and an instruction acquiring unit 140. The data acquiring unit 110 includes an image acquiring unit 111. The image processing unit 130 includes an alignment unit 131, an individual image determination unit 132, an image group determination unit 133, an instructing unit 134, and a display control unit 135. Further, the instructing unit 134 includes an image re-capturing necessity instructing unit 1341.

(SLO Image Capturing Apparatus Equipped with an Adaptive Optical System)

Figure 3:
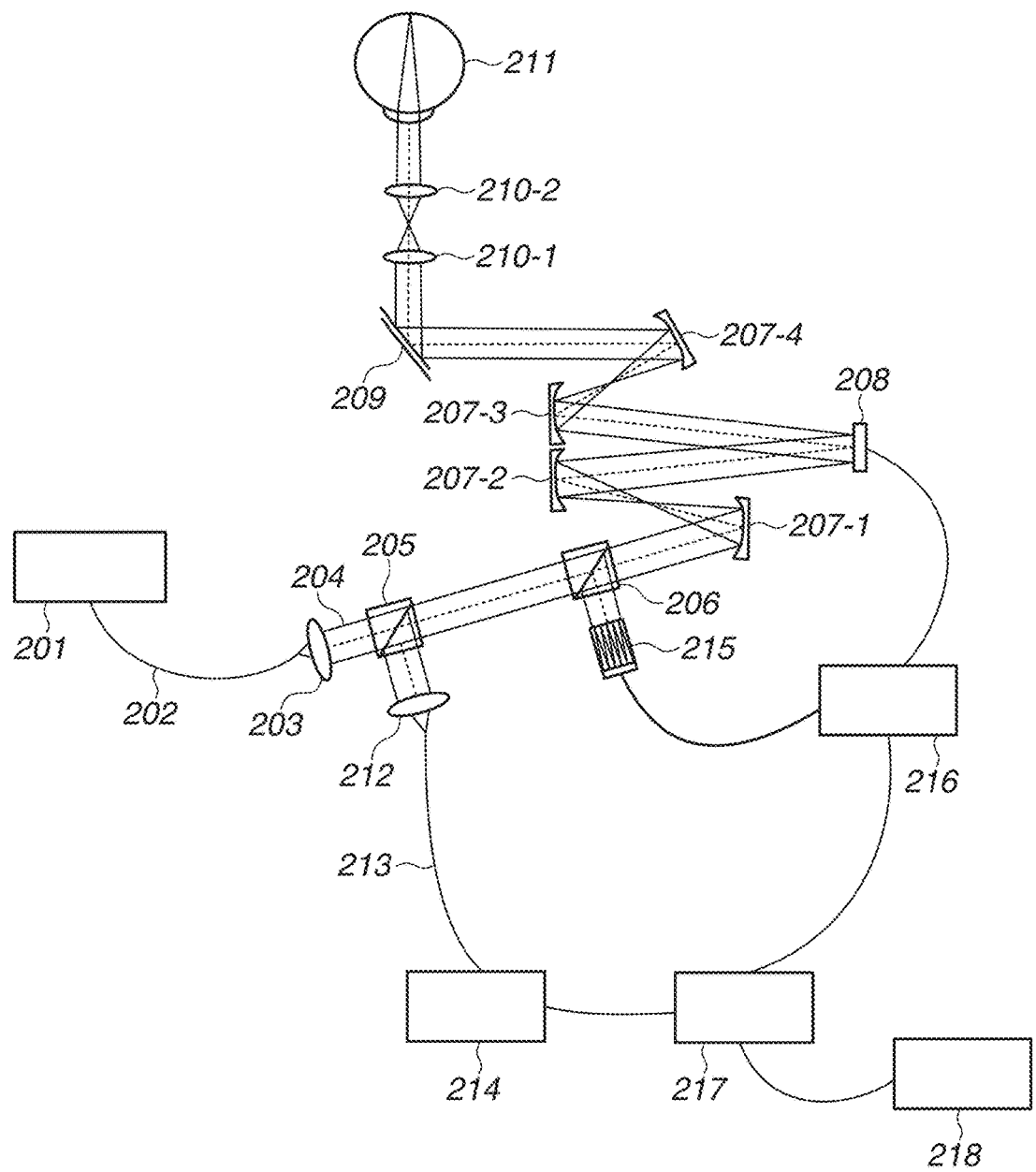
FIG. 3 illustrates an entire configuration of an SLO image capturing apparatus according to an exemplary embodiment of the present invention.

Next, a configuration of the SLO image capturing apparatus 20 including an adaptive optical system will be described with reference to FIG. 3. A light source 201 is a super luminescent diode (SLD) light source. In the present exemplary embodiment, the light source 201 can be commonly used for eye fundus image capturing and for wavefront measurement. Alternatively, it is useful to provide an independent light source dedicated to the eye fundus imaging and another independent light source dedicated to the wavefront measurement. In this case, the system can be configured in such a way as to multiplex light beams emitted from respective light sources at an intermediate position. The light from the light source 201 reaches a collimator 203 via a single-mode optical fiber 202. The light travels as parallel measurement light 205 from the collimator 203. The parallel measurement light 205 reaches and passes through a light dividing unit 204. The light dividing unit 204 is constituted by a beam splitter. Then, the light is guided into the adaptive optical system.

The adaptive optical system includes a light dividing unit 206, a wavefront sensor 215, a wavefront correcting device 208, and reflecting mirrors 207-1 to 207-4 provided to guide the light to them. In this case, the reflection mirrors 207-1 to 207-4 are positioned in such a manner that at least a pupil of an eye is conjugate with the wavefront sensor 215 and the wavefront correcting device 208 optically. In the present exemplary embodiment, the light dividing unit 206 is a beam splitter. Further, the wavefront correcting device 208 according to the present exemplary embodiment is a spatial phase modulator including a liquid crystal element. As another embodiment, the wavefront correcting device 208 can be constituted by a variable shape mirror. The light having passed through the adaptive optical system is scanned one-dimensionally or two-dimensionally by a scanning optical system 209. The scanning optical system 209 employed in the present exemplary embodiment includes two Galvano scanners, one of which is dedicated to main scanning (to be performed in the horizontal direction of the eye fundus) and the other of which is dedicated to sub scanning (to be performed in the vertical direction of the eye fundus). Alternatively, to realize a high-speed photographing operation, the scanning optical system 209 can be configured to include a resonance scanner for the main scanning. The measurement light 205 scanned by the scanning optical system 209 travels through two eyepiece lenses 210-1 and 210-2 and reaches an eye 211. The measurement light 205 is then reflected or scattered by the eye fundus. The position of each eyepiece lens 210-1 or 210-2 is adjustable to optimize the irradiation according to the diopter of the eye 211. As another example, the eyepiece lens used in the above-mentioned configuration can be replaced by a spherical mirror.

The return light, i.e., the light reflected or scattered by the retina of the eye 211, travels in an opposite direction along a path similar to the above-mentioned path. The light dividing unit 206 reflects a part of the return light toward the wavefront sensor 215 that can measure the wavefront of input light. The wavefront sensor 215 is connected to an adaptive optics control unit 216 and transmits the wavefront of the input light to the adaptive optics control unit 216. The wavefront correcting device 208 is also connected to the adaptive optics control unit 216. The wavefront correcting device 208 can perform modulation according to an instruction from the adaptive optics control unit 216. The adaptive optics control unit 216 calculates a modulation amount (i.e., a correction amount) to obtain a wavefront having no aberration based on the wavefront acquired based on a measurement result of the wavefront sensor 215. Then, the adaptive optics control unit 216 instructs the wavefront correcting device 208 to perform modulation according to the calculated modulation amount. The adaptive optics control unit 216 repetitively performs processing for the wavefront measurement and the instruction to the wavefront correcting device 208 in such a way as to perform a feedback control to optimize the wavefront constantly.

The light dividing unit 204 reflects a part of the return light having passed through the light dividing unit 206. The reflected return light reaches a light intensity sensor 214 via a collimator 212 and an optical fiber 213. The light intensity sensor 214 converts input light into an electric signal. A control unit 217 generates an eye image based on the electric signal received from the light intensity sensor 214. A display device 218 displays the eye image generated by control unit 217. If the scanning optical system illustrated in FIG. 3 is configured to have an increased swing angle and the adaptive optics control unit 216 is prevented from performing the aberration correction, the SLO image capturing apparatus 20 can operate as an ordinary SLO apparatus and can capture a wide viewing angle SLO image (i.e., the wide viewing angle image Dl).

(Hardware Configuration and Execution Procedure of the Ophthalmologic Apparatus 10)

Figure 4:
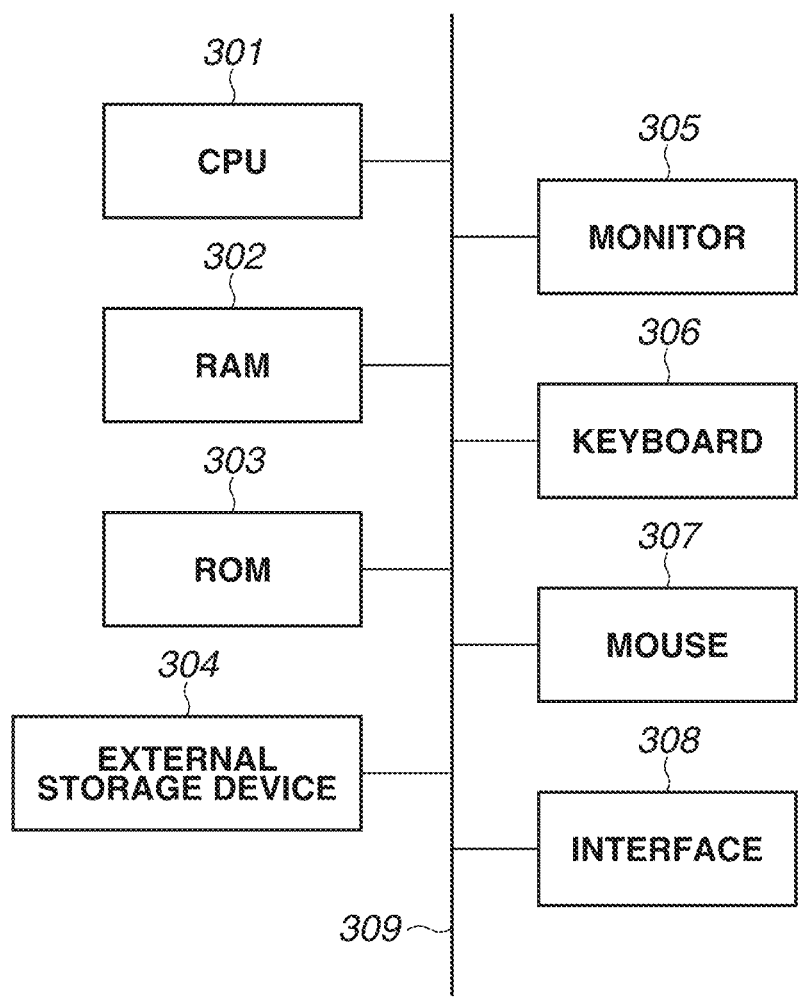
FIG. 4 is a block diagram illustrating a hardware configuration of a computer that includes a hardware part capable of functionally operating as a storing unit and an image processing unit and a software part capable of serving as the other units.

Next, a hardware configuration of the ophthalmologic apparatus 10 will be described in detail below with reference to FIG. 4. The hardware configuration illustrated in FIG. 4 includes a central processing unit (CPU) 301, a memory (RAM) 302, a control memory (ROM) 303, an external storage device 304, a monitor 305, a keyboard 306, a mouse 307, and an interface 308. A control program that can realize image processing functions according to the present exemplary embodiment and relevant data to be used when the control program is executed are stored in the external storage device 304. The control program and the relevant data can be appropriately loaded into the RAM 302 via a bus 309 under the control of the CPU 301 and can be executed or processed by the CPU 301, so that each functional unit described below can be realized. Various functions of respective blocks constituting the ophthalmologic apparatus 10 will be described in detail below with reference to a flowchart illustrated in FIG. 5, which is a practical execution procedure of the ophthalmologic apparatus 10.

<Step S510: Image Acquisition Pattern Selection>

The ophthalmologic apparatus 10 acquires information about a predetermined image acquisition pattern (e.g., photographing position or angle of view) having been selected by a user, via the instruction acquiring unit 140. In the present exemplary embodiment, the ophthalmologic apparatus 10 sets the fixation target positions Fl and Fh to a fovea centralis of a macula and acquires the wide viewing angle image Dl and the high magnification images Dhj illustrated in FIG. 6H. The photographing position setting method is not limited to the above-mentioned example. The fixation target positions Fl and Fh can be set arbitrarily.

<Step S520: Image Acquisition>

The image acquiring unit 111 requests the SLO image capturing apparatus 20 to acquire the wide viewing angle image Dl, the high magnification images Dhj, and the corresponding fixation target positions Fl and Fh. In response to the acquisition request, the SLO image capturing apparatus 20 acquires and transmits the wide viewing angle image Dl, the high magnification images Dhj, and the corresponding fixation target positions Fl and Fh. The image acquiring unit 111 receives the wide viewing angle image Dl, the high magnification images Dhj, and the fixation target positions Fl and Fh from the SLO image capturing apparatus 20 via the LAN 30. The image acquiring unit 111 stores the received data in the storing unit 120. In the present exemplary embodiment, the wide viewing angle image Dl and the high magnification images Dhj are moving images whose inter-frame alignment is already completed.

<Step S530: Alignment>

The alignment unit 131 performs the alignment of the high magnification images Dhj relative to the wide viewing angle image Dl and obtains a relative position of each high magnification images Dhj on the wide viewing angle image Dl. If there is any overlapping region between the high magnification images Dhj, the alignment unit 131 calculates a similarity between images, of the overlapping region. Then, the alignment unit 131 aligns the positions of respective high magnification images Dhj in such a way as to maximize the similarity between images.

Next, in a case where the images acquired in step S520 include two or more images that are mutually different in magnification, the alignment unit 131 prioritizes the alignment of a lower magnification image. For example, in a case where the acquired images include the high magnification image D1j and the intermediate-magnification image D2k, the alignment unit 131 first performs the alignment of the intermediate-magnification image D2k relative to the wide viewing angle image Dl. Subsequently, the alignment unit 131 performs the alignment of the high magnification image D1j relative to the intermediate-magnification image D2k. If only the high magnification image is acquired in step S520, the alignment unit 131 performs the alignment of the high magnification images Dhj relative to the wide viewing angle image Dl. The alignment unit 131 acquires the fixation target position Fh used in the photographing operation of the high magnification images Dhj from the storing unit 120. The alignment unit 131 uses the acquired fixation target position Fh in setting an initial search point of an alignment parameter to be referred to in the alignment between the wide viewing angle image Dl and the high magnification images Dhj. Further, any other conventionally known methods can be used arbitrarily in checking the similarity between images or performing the coordinate conversion. The similarity between images used in the present exemplary embodiment is a correlation coefficient. The coordinate conversion method used in performing the alignment is Affine conversion.

<Step S540: Individual Image Conformity Determination>

The individual image determination unit 132 performs conformity determination processing based on a luminance value of each frame and an inter-frame movement amount.

First, the individual image determination unit 132 acquires conformity determination criteria that have been acquired via the instruction acquiring unit 140.

The determination criteria include the following items a) to d).

a) The luminance value of the image is within an adequate range.
b) The image quality (e.g., S/N ratio or number of images to be superimposed) is within an adequate range.
c) The movement amount relative to a reference frame is within an adequate range.
d) The focus position is within an adequate range.

In the present exemplary embodiment, the individual image determination unit 132 checks the conformity with reference to the criteria a) and b). Specifically, the criterion is the number of superimposable frames that do not include any low-luminance frame that may occur due to nictitation. The individual image determination unit 132 determines the above-mentioned conformity for the high-magnification SLO image Dhj. Further, in a case where the conformity satisfies the predetermined criteria, the image processing unit 130 forms an individual image through superimposing processing. The individual image to be obtained in this case can be an image obtainable by superimposing all of frames that cooperatively constitute a moving image or can be a single selected frame. Further, the individual image can be an image obtainable by superimposing only selected images that are relatively low in noise. In the present exemplary embodiment, the high magnification image is a moving image of visual cells as illustrated in FIG. 6C. The image processing unit 130 forms a composite image by superimposing only the regions having positive pixel values in all frames satisfying the above-mentioned condition a). Accordingly, for example, in a case where the positions of respective frames of the individual high-magnification moving image are associated with each other as illustrated in FIG. 6C (Nf: frame number), FIG. 6D illustrates a result of the superimposing processing. According to the above-mentioned example, a head frame is assumed as the reference frame. A black color region illustrated in FIG. 6D is a region that has not been used in the superimposing processing (i.e., an image missing region).

<Step S545: Image Re-Capturing Necessity Instruction>

The image re-capturing necessity instructing unit 1341 instructs the image acquiring unit 111 about the necessity of re-capturing the corresponding high magnification image Dhj based on the individual image conformity determined in step S540. Specifically, if the individual image conformity does not satisfy the predetermined criteria (YES in step S545), the operation returns to step S520. For example, when the number of images to be superimposed does not satisfy a threshold value Tf, the image re-capturing necessity instructing unit 1341 determines that the image re-capturing is necessary. In this case, the image re-capturing necessity instructing unit 1341 instructs the image acquiring unit 111 to perform image re-capturing processing. If the individual image conformity satisfies the predetermined criteria (NO in step S545), the operation proceeds to step S550. Further, the instructing unit 134 is functionally operable as the determination unit configured to determine photographing conditions for capturing images at different positions of an eye based on the characteristic continuity between a plurality of images.

<Step S550: Determining Whether the Image Group has been Entirely Obtained>

The ophthalmologic apparatus 10 determines whether the image group of the image acquisition pattern acquired in step S510 has been entirely obtained. If it is determined that the image group has been entirely obtained (YES in step S550), the operation proceeds to step S560. If it is determined that there is any image that has not yet been obtained (NO in step S550), the operation returns to step S520.

<Step S560: Image Group Conformity Determination Processing>

The image group determination unit 133 forms a composite of a plurality of images constituting the image group formed in step S540, which neighbor each other at different positions, based on the alignment parameter obtained in step S530. Then, the image group determination unit 133 determines the image group conformity based on the relative position and the luminance continuity of the image group. However, as another example, the image group determination unit 133 can refer to either the relative position or the luminance characteristics in determining the image group conformity. If the image group conformity does not satisfy the predetermined criteria, the instructing unit 134 instructs the image acquiring unit 111 to perform the image re-capturing processing. In the present exemplary embodiment, the image group is composed of nine superimposed images as illustrated in FIG. 6G. An image number j is initially set on an upper-left image. The image number j increments successively according to the raster scanning (i.e., zigzag scanning) order.

The following is a determination policy with respect to the conformity of the image composite (i.e., the image group), more specifically, the image group conformity required to observe the entire image composite under the same conditions.

1. The image composite does not include any image missing region (in other words, the luminance does not change discontinuously).
2. The image quality is stable irrespective of photographing position.

In this case, if the necessity of performing the image re-capturing processing is determined based on only the conformity of an individual image, instead of determining the image group conformity, strictly determining whether an imaging target region has been acquired will be necessary for each image. As a result, the instruction of the image re-capturing will be frequently given. In this case, it will be necessary to set a wider overlapping region (i.e., increase the number of image pickup positions) to prevent the image re-capturing determination from increasing. Therefore, efficiently acquiring a high-magnification image group satisfying the above-mentioned conditions 1 and 2 is feasible when the continuity or the subsidiarity of data in the edge portion or the overlapping region between neighboring images is taken into consideration in the conformity determination. Specifically, in the present exemplary embodiment, there is an overlapping region between two neighboring images (e.g., a gray region illustrated in FIG. 6F) or an overlapping region between four neighboring images (e.g., a black region illustrated in FIG. 6F). Even in a case where a single image includes an image missing region, if there is any data obtainable from the overlapping region between neighboring images, it is determined that the image group does not include any image missing region. Therefore, the image group conformity is determined according to the following procedure.

More specifically, the image group conformity determination procedure includes:

(1) forming a matrix-like composite composed of the individual images generated in step S540 according to the alignment parameter obtained in step S530;

(2) completing the formation of the image composite immediately if there is not any image missing region; and
(3) identifying the position of each image missing region if the image missing region is present, and obtaining a number list of the image to which the image missing region belongs.

For example, according to the example illustrated in FIG. 6G, each of images 6 and 9 includes an image missing region that has been caused through the above-mentioned composite processing. Therefore, the number list of each image including the image missing region is obtained.

The procedure further includes:
(4) calculating the image group conformity according to the following formula.

Formula:
(Total number of composite images−Number of images including any image missing region)/ (Total number of composite images)

<Step S565: Image Re-Capturing Necessity Instruction>

If it is determined that the determined image group conformity is less than 1 (YES in step S565), the image re-capturing necessity instructing unit 1341 instructs the image acquiring unit 111 to perform the image acquisition processing for the image that includes the image missing region. Then, the operation returns to step S520. If it is determined that the image group conformity is equal to 1 (NO in step S565), the operation proceeds to step S570.

<Step S570: Display>

If the image group conformity is equal to 1, the image processing unit 130 performs image group formation processing. The display control unit 135 causes the monitor 305 to display the formed image group (i.e., image composite). Specifically, the image processing unit 130 performs the image group formation processing according to the following procedure.

The procedure includes (5) acquiring a value ANmin that represents the number of superimposed frames that cooperatively constitute a superimposing image smallest in the number of superimposed frames, in the group of superimposing images obtained through the individual image formation processing. In addition, the procedure includes setting the value ANmin as the number of images constituting the image composite and changing the number of frames to be superimposed at each photographing position to ANmin to generate a superimposing image. In this case, the image processing unit 130 starts, from the head of the frame group, selecting ANmin sheets of frames that can satisfy the criterion (a) relating to the luminance value in step S540 and generates a superimposing image based on the selected frames. The frame selection method is not limited to the above-mentioned example and any other arbitrary selection method is usable.

The image group conformity determination procedure further includes (6) generating an image composite using the superimposing images having been generated in the above-mentioned process (5).

Figure 6H:
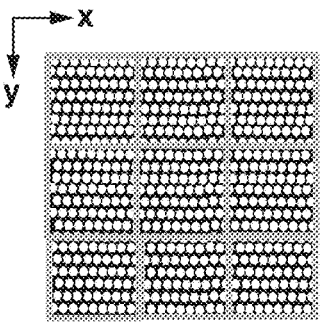

(FIG. 6H Illustrates an Image Composite Having been Obtained Through the Image Re-Capturing Processing, which is Identical in the Number of Superimposing Images and does not Include any Image Missing Region)

The display control unit 135 causes the monitor 305 to display the formed image group. In a case where a plurality of high magnification images Dhj is already acquired, the display control unit 135 can correct any difference in concentration, if it appears, between the high-magnification images before performing the above-mentioned display processing. In this case, a conventionally known luminance correction method can be arbitrarily used. In the present exemplary embodiment, the display control unit 135 generates a histogram Hj in each of the high magnification images Dhj and corrects the concentration difference by linearly converting the luminance value of each high magnification image Dhj in such a manner that the high magnification images Dhj can possess common values with respect to the average and dispersion of the histogram Hj. The luminance correction method for high-magnification images is not limited to the above-mentioned example and any other conventionally known luminance correction method can be arbitrarily used. Further, regarding the display magnification, if a high magnification image is designated by an operator via the instruction acquiring unit 140, the display control unit 135 causes the monitor 305 to displays an image obtained by enlarging the high magnification image.

In the present exemplary embodiment, the high magnification image display by the monitor 305 is performed after completing the acquisition of all images. However, the present invention is not limited to the above-mentioned example. For example, it is feasible for the display control unit 135 to cause the monitor 305 to display each individual image upon completing the acquisition of the individual image. Further, after determining the conformity of each individual image, the display control unit 135 can cause the monitor 305 to display the determination result together with a formed image so that image capturing results can be sequentially confirmed. In this case, if there is an image that is determined as being low in conformity and requiring the image re-capturing processing, the display control unit 135 can cause the monitor 305 to perform an arbitrary discriminable display (e.g., giving color to a corresponding image pickup region or a frame thereof).

<Step S575: Instruction on Whether to Store the Result>

The instruction acquiring unit 140 acquires an instruction from an external device to determine whether to store, in the data server 40, the wide viewing angle image Dl, the high magnification images Dhj, the fixation target positions Fl and Fh, the alignment parameter value acquired in step S530, and the image composite formed in step S570. The above-mentioned instruction can be input by an operator, for example, via the keyboard 306 or the mouse 307. If the instruction acquiring unit 140 acquires the storing instruction (YES in step S575), the operation proceeds to step S580. If the instruction acquiring unit 140 does not acquire the storing instruction (NO in step S575), the operation proceeds to step S585.

<Step S580: Storing of Result>

The image processing unit 130 associates examination date and time, information about identifying eye to be examined, the wide viewing angle image Dl, the high magnification images Dhj, the fixation target positions Fl and Fh, the alignment parameter value, and the image composite with each other. Then, the image processing unit 130 transmits the associated data to the data server 40.

<Step S585: Instruction on Whether to Terminate the Processing>

Figure 2B:
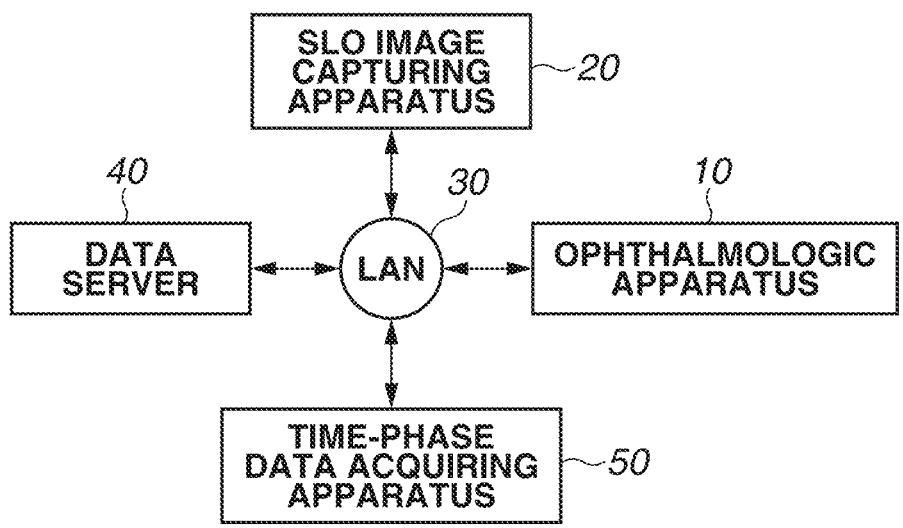
Figure 6I:
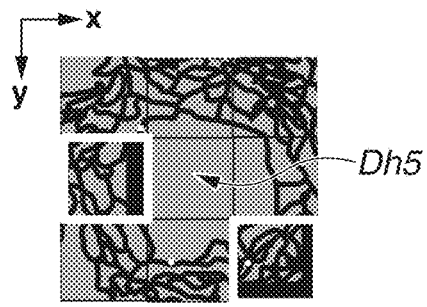
Figure 6J:
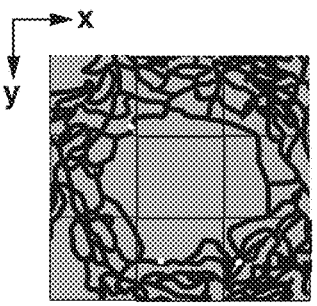

The instruction acquiring unit 140 acquires an instruction from an external device to determine whether to cause the ophthalmologic apparatus 10 to terminate the processing relating to the wide viewing angle image Dl and the high magnification images Dhj. The above-mentioned instruction can be input by an operator via the keyboard 306 or the mouse 307. If the instruction acquiring unit 140 acquires a processing termination instruction (YES in step S585), the ophthalmologic apparatus 10 terminates the processing. On the other hand, if the instruction acquiring unit 140 acquires a processing continuation instruction (NO in step S585), the operation returns to step S510 to perform processing for an eye to be next examined (or repeat the processing for the same eye to be examined). In the present exemplary embodiment, the image composite to be formed based on the determination of the image group conformity is a composite of still images (i.e., superimposing images). However, the present invention is not limited to the above-mentioned example. For example, it is useful that data subsidiarity at an edge portion or an overlapping region between neighboring moving images is taken into consideration in determining the conformity and a moving image composite is displayed as illustrated in FIG. 6J. Basic processing for displaying a composite of moving images is similar to that for displaying a composite of still images and different in the following points. More specifically, the image group formation processing includes (i) connecting a time-phase data acquiring apparatus 50 to the ophthalmologic apparatus 10 as illustrated in FIG. 2B. The time-phase data acquiring apparatus 50 acquires time-phase data and a moving image simultaneously. For example, the time-phase data is biological signal data acquired by a pulse wave detector. The reproduction period of each moving image can be obtained by referring to the time-phase data. In this case, the time-phase data acquiring apparatus 50 performs frame interpolation processing on moving images to eliminate any difference in the reproduction period.

The image group formation processing further includes (ii) obtaining the number of frames belonging to the longest consecutive frames section that do not include any luminance abnormal frame, in conformity determination processing for each photographing position. If the obtained number of frames does not satisfy a predetermined level, the instructing unit 134 instructs the image acquiring unit 111 to perform the image re-capturing processing.

The image group formation processing further includes (iii) performing image group conformity determination processing according to the following policy.

1. The image composite does not include any image missing region.
2. The number of reproduction frames is substantially the same at each photographing position.

(iv) The frames selected in the above-mentioned process (5) of the image group formation processing are frames in a consecutive frame section.

Through the above-mentioned processing, it is feasible to display a composite of moving images that does not include any image missing region. It becomes feasible to form the composite of moving images by using frames that are consecutive and identical in the number of reproduction frames. In a case where there is not any time-phase data having been already acquired, it is feasible to display the image composite without performing any adjustment with respect to reproduction time and reproduction period.

According to the above-mentioned configuration, the ophthalmologic apparatus 10 captures a group of adaptive optics SLO moving images at different photographing positions and then compares a composite of the acquired images with an imaging target region. The ophthalmologic apparatus 10 determines the image group conformity by checking the presence of a non-observable region based on the image feature amount. If there is any image whose conformity does not satisfy the predetermined level, the ophthalmologic apparatus 10 instructs the image acquiring unit to perform the image re-capturing processing. Through the above-mentioned processing, in a case where an observation target cell group (or tissue) and a lesion thereof extend beyond the acquisition positions of a plurality of high magnification images, it becomes feasible to capture a group of observable images under substantially the same conditions.

[Image Feature Continuity of a Plurality of Images Photographed at Different Positions]

A second exemplary embodiment will be described in detail below. An ophthalmologic apparatus according to the second exemplary embodiment is different from the ophthalmologic apparatus according to the first exemplary embodiment characterized by determining the image group conformity based on the presence of any image missing part in an imaging target region (e.g., a relative position or continuity in luminance characteristics between the images constituting the image group). The ophthalmologic apparatus according to the second exemplary embodiment is configured to determine the image group conformity based on image feature continuity extracted from neighboring high magnification images. Specifically, the ophthalmologic apparatus according to the second exemplary embodiment determines the image group conformity based on the continuity of a capillary region of a parafovea extracted from high-magnification SLO images.

The configuration of each device connected to an ophthalmologic apparatus 10 according to the present exemplary embodiment is similar to that described in the first exemplary embodiment. In the present exemplary embodiment, the data server 40 can store normal values representing eye image features and distributions thereof in addition to acquisition condition data (e.g., wide viewing angle image Dl, high magnification images Dh, and fixation target positions Fl and Fh) used in an image acquiring operation for each examinee's eye. The eye image features to be processed in the present exemplary embodiment include the retina blood vessel, the capillary Q, and the blood corpuscle W, although any arbitrary eye image feature is usable. The data server 40 stores the eye image features output from the ophthalmologic apparatus 10. Further, in response to a request from the ophthalmologic apparatus 10, the data server 40 can transmit the normal value data relating to eye image features and distributions thereof to the ophthalmologic apparatus 10.

Figure 7:
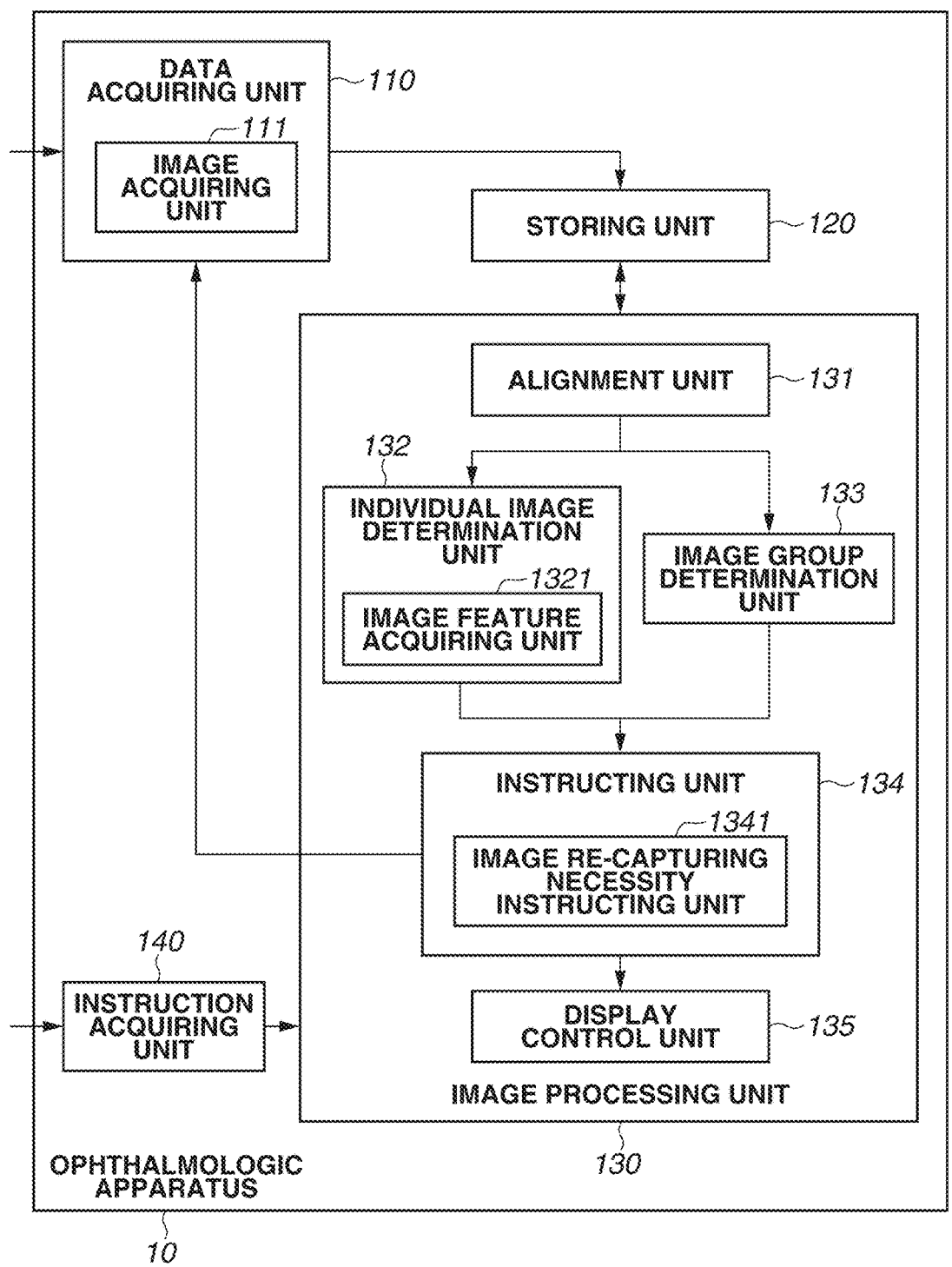
FIG. 7 is a block diagram illustrating a functional configuration of an ophthalmologic apparatus according to a second exemplary embodiment of the present invention.

FIG. 7 is a diagram illustrating functional blocks of the ophthalmologic apparatus 10 according to the present exemplary embodiment. The ophthalmologic apparatus 10 illustrated in FIG. 7 is different from that described in the first exemplary embodiment in that the individual image determination unit 130 includes an image feature acquiring unit 1321. Further, an image processing flow according to the present exemplary embodiment is similar to that illustrated in FIG. 5. Processing to be performed in step S510, step S520, step S530, step S550, step S575, step S580, and step S585 is similar to the processing described in the first exemplary embodiment. Therefore, in the present exemplary embodiment, processing to be performed in step S540, step S545, step S560, step S565, and step S570 will be described in detail below.

<Step S540: Conformity Determination Processing Performed for Each of Images Captured at Different Positions>

The individual image determination unit 132 performs individual image conformity determination processing. The determination criteria, to be referred to in determining the individual image conformity, can include the following condition e) in addition to the above-mentioned conditions a) to d) in step S540 of the first exemplary embodiment.

e) Image feature acquired by the image feature acquiring unit 1321.

The above-mentioned image feature is, for example, the number of pixels constituting the image feature, area ratio to the image constituted by the above-mentioned pixels, or contrast in case of multi-value data. In the present exemplary embodiment, the image feature is used in only the image group conformity determination. More specifically, similar to the first exemplary embodiment, the number of frames that are not abnormal in luminance is referred to as the individual image conformity. Further, in the present exemplary embodiment, the high magnification image is a moving image obtained by photographing a capillary. An image of a capillary region extracted from the moving image (hereinafter, referred to as "capillary image") is formed. Further, in a case where the individual image conformity satisfies the predetermined criteria, the image feature acquiring unit 1321 extracts the capillary region by using only positive pixel value regions in all frames except for the luminance abnormal frames. More specifically, in the high magnification images Dhj, the image feature acquiring unit 1321 identifies a blood corpuscle component moving range as the capillary region according to the following procedure.

(a) The image feature acquiring unit 1321 performs subtraction processing on neighboring frames of the high magnification images Dhj whose inter-frame alignment is already completed (generates a differential moving image).

(b) The image feature acquiring unit 1321 calculates a luminance statistic amount (dispersion) relating to the frame direction at each x-y position of the differential moving image generated in the above-mentioned process (a).

(c) The image feature acquiring unit 1321 identifies a region in which the luminance dispersion is equal to or greater than a threshold value Tv, at each x-y position of the differential moving image, as a blood corpuscle moving region, more specifically, as the capillary region.

The capillary detection processing method is not limited to the above-mentioned method. Any other conventionally known method can be arbitrarily used. For example, it is useful to detect a blood vessel by applying a filter capable of intensifying a linear structure to a specific frame of the high magnification images Dhj.

Next, the image feature acquiring unit 1321 detects the boundary of a non-blood vessel region from the obtained capillary region. There is a region that does not include any blood vessel (i.e., the non-blood vessel region) in the vicinity of a fovea centralis of a retina (see Dh5 in FIG. 6I). An initial lesion of a retina blood vessel tends to appear near the boundary of the non-blood vessel region. The non-blood vessel region tends to expand accompanying the progress of a disease (e.g., diabetic retinopathy). Accordingly, the non-blood vessel region boundary is an important target in observation and analysis. In the present exemplary embodiment, the image feature acquiring unit 1321 disposes a circular variable shape model on a high magnification image Dh5 positioned at the center of a high magnification image group. The image feature acquiring unit 1321 identifies the non-blood vessel region by deforming the shape model in such a way as to coincide with the non-blood vessel region boundary. The image feature acquiring unit 1321 designates the position of the deformation completed variable shape model as a candidate position of the non-blood vessel region boundary. However, the non-blood vessel region boundary identification method is not limited to the above-mentioned example. Any other conventionally known method can be arbitrarily used.

<Step S545: Image Re-Capturing Necessity Instruction>

The image re-capturing necessity instructing unit 1341 instructs the image acquiring unit 111 about the necessity of re-capturing the corresponding high magnification image Dhj based on the individual image conformity determined in step S540. Specifically, if the individual image conformity does not satisfy the predetermined criteria (YES in step S5454), the operation returns to step S520. For example, when the number of frames whose luminance is not abnormal does not satisfy a threshold value Tf, the image re-capturing necessity instructing unit 1341 determines that the image re-capturing is necessary. In this case, the image re-capturing necessity instructing unit 1341 instructs the image acquiring unit 111 to perform the image re-capturing processing. If the individual image conformity satisfies the predetermined criteria (NO in step S545), the operation proceeds to step S550.

<Step S560: Image Group Conformity Determination Processing>

Figure 8A:
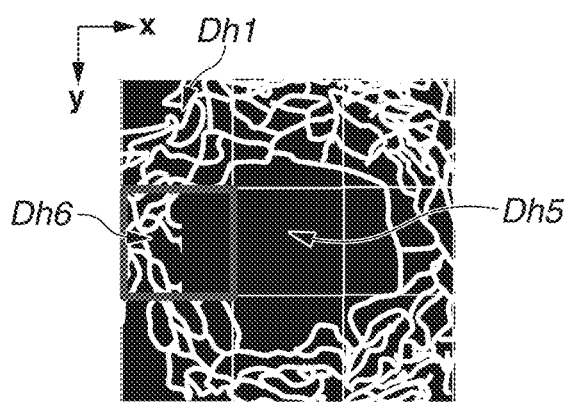
FIGS. 8A, 8B, 8C, 8D, 8E, and 8F illustrate the contents of image processing according to the second exemplary embodiment of the present invention.

The image group determination unit 133 forms a matrix-like composite of the image group (capillary image group) generated based on the image feature acquired by the image feature acquiring unit 1321 based on the alignment parameter obtained in step S530. Then, the image group determination unit 133 determines the conformity based on the continuity of the image feature (i.e., the capillary region). If the image group conformity does not satisfy the predetermined criteria, the instructing unit 134 instructs the image acquiring unit 111 to perform the image re-capturing processing. In the present exemplary embodiment, the capillary image group is composed of nine capillary images as illustrated in FIG. 8A. The image number j is initially set on an upper left image. The image number j increments successively according to the raster scanning (i.e., zigzag scanning) order.

More specifically, the image group conformity determination procedure includes:

(1') montaging (forming an image composite) (collectively patching) the capillary images generated in step S540 according to the alignment parameter obtained in step S530;

(2') completing the formation of the image composite immediately if there is not any image feature missing region; and (3') identifying the position of each image feature missing region if the image feature missing region is present, and obtaining a number list of the image to which the image feature missing region belongs.

For example, according to the example illustrated in FIG. 8A, an image 6 includes an image feature missing region that has been caused by the composite processing. Therefore, the image group determination unit 133 obtains a number list of the image including the image feature missing region.

(4') The image group determination unit 133 calculates the following index with respect to the image feature (i.e., the capillary region) acquired from the high magnification images Dhj and determines the image group conformity based on a calculated index value.

(Sum of lengths of actually acquired non-blood vessel region boundaries)/(Sum of lengths of the sequences of points representing the non-blood vessel region boundary candidate having been set in step S540)

If the determined image group conformity is less than a predetermined value (e.g., 1 in the present exemplary embodiment), the instructing unit 134 instructs the image acquiring unit 111 to re-capture an image of a defective part including the image feature missing region. Then, the operation returns to step S520. If the image group conformity satisfies the predetermined value (NO in step S565), the operation proceeds to step S570.

<Step S570: Display>

If the image group conformity satisfies the predetermined value, the image processing unit 130 performs image group formation processing. The display control unit 135 causes the monitor 305 to display the formed image group (i.e., image composite). Specifically, the image processing unit 130 performs the image group formation processing according to the following procedure. The procedure includes (5') acquiring a value ANmin' that represents the number of frames used in the generation of a capillary image smallest in the number of frames used in the capillary extraction, in the group of capillary images obtained through the individual image formation processing. In addition, the procedure includes setting the value ANmin' as the number of frames to be used in constituting each capillary image and changing the number of frames to be used in the capillary extraction at each photographing position to ANmin' to generate a capillary image again.

Figure 8B:
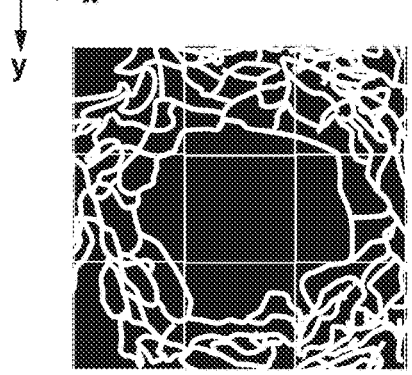

In this case, the image processing unit 130 starts, from the head of the frame group, selecting ANmin' sheets of frames that can satisfy the criterion (a) relating to the luminance value in step S540 and generates a capillary image based on the selected frames. The frame selection method is not limited to the above-mentioned example and any other arbitrary selection method is usable. The procedure further includes (6') generating an image composite using the capillary images generated in the above-mentioned process (5'). (FIG. 8B illustrates a result of the image re-capturing processing, which does not include any image feature missing region. The obtained image composite remains the same with respect to the number of frames to be used in the capillary extraction.)

Figure 8C:
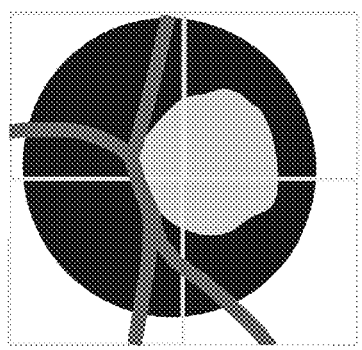

The display control unit 135 displays the image composite of the capillary images using the alignment parameter value obtained in step S530. In the present exemplary embodiment, the display control unit 135 displays a matrix-like composite composed of the extracted capillary images as illustrated in FIG. 8B. In the present exemplary embodiment, the display of high magnification images and feature extraction images (i.e., capillary images) on the monitor 305 does not starts before completing the acquisition of all images. However, the present invention is not limited to the above-mentioned example. For example, the display control unit 135 can be configured to cause the monitor 305 to display each individual image immediately after the individual image is acquired, or display a formed individual image together with a result of the individual image conformity determination, so that image capturing results can be sequentially confirmed. In this case, if there is an image that is determined as being low in conformity and requiring the image re-capturing processing, the display control unit 135 can cause the monitor 305 to perform an arbitrary discriminable display (e.g., giving color to a corresponding image pickup region or a frame thereof). Further, the image feature to be used to calculate the image group conformity is not limited to the capillary region or the non-blood vessel region boundary. Any other arbitrary image feature can be used. For example, in a case where the ophthalmologic apparatus determines the image group conformity based on four sheets of high magnification images obtained by photographing an optic papilla as illustrated in FIG. 8C, the ophthalmologic apparatus can detect a recessed portion through threshold value processing and can determine the image group conformity based on the continuity of the recessed portion at a boundary position thereof. Specifically, the ophthalmologic apparatus can calculate the image group conformity according to the following formula.

Formula: (Sum of edge pixels which are a part of the edge pixels belonging to the recessed portion boundary and 2 in the number of connecting components (i.e., neighboring edge pixels))/(Sum of edge pixels belonging to the recessed portion boundary)

Figure 8D:
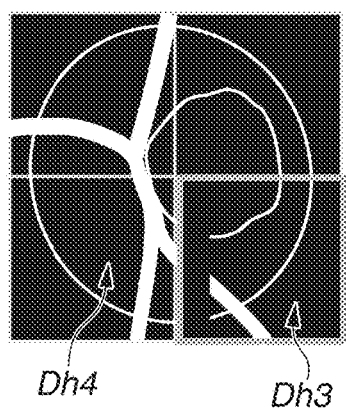
Figure 8E:
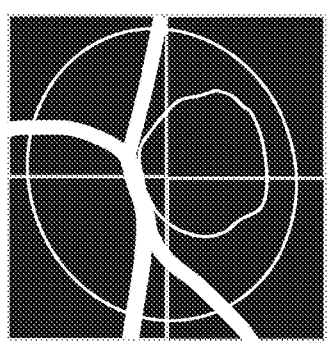
Figure 8F:
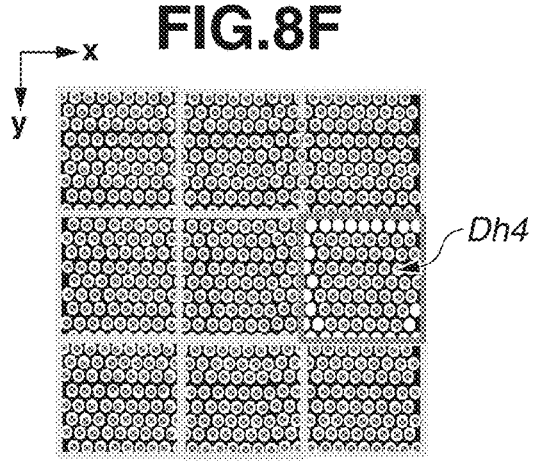

The image group conformity is not limited to the above-mentioned example. For example, the ophthalmologic apparatus can refer to an area of the recessed portion detected through the threshold value processing. If the image group conformity is less than 1, the instructing unit 134 instructs the image acquiring unit 111 to re-capture an image of a defective part including the image feature missing region (i.e., an image having an edge pixel whose number of connecting components is 1, namely Dh3). The image acquiring unit 111 performs image re-capturing processing. Through the above-mentioned image group conformity determination and the image re-capturing processing, it becomes feasible to obtain an image composite that does not include any discontinuous portion as illustrated in FIG. 8E, which is apparently excellent compared to the image composite illustrated in FIG. 8D that includes an image feature discontinuous portion in the lower-right high magnification image Dh3. Analyzing an analysis target tissue under substantially the same condition is feasible. Further, in a case where visual cells are photographed as illustrated in FIG. 8F, the image group conformity can be determined according to the following procedure. The procedure includes detecting each visual cell with reference to a peak pixel value in the high magnification image. The procedure further includes measuring the number of the detected visual cells or the density of the visual cells for each image or each sub block of the image, thereby determining the image group conformity.

According to the above-mentioned configuration, the ophthalmologic apparatus 10 determines the image group conformity based on the image feature continuity extracted from neighboring high magnification images. Through the above-mentioned processing, in a case where an analysis target cell group (or tissue) and a lesion thereof extend beyond the acquisition positions of a plurality of high magnification images, it becomes feasible to capture a group of analyzable images under substantially the same conditions. The conditions to be referred to in determining the image group conformity can include at least one of the conditions described in the first exemplary embodiment (i.e., the relative position and the luminance characteristics of the image group) in addition to the image feature.

[Determining the Image Group Conformity in Response to Acquisition of Each Image at Different Positions]

Figure 9:
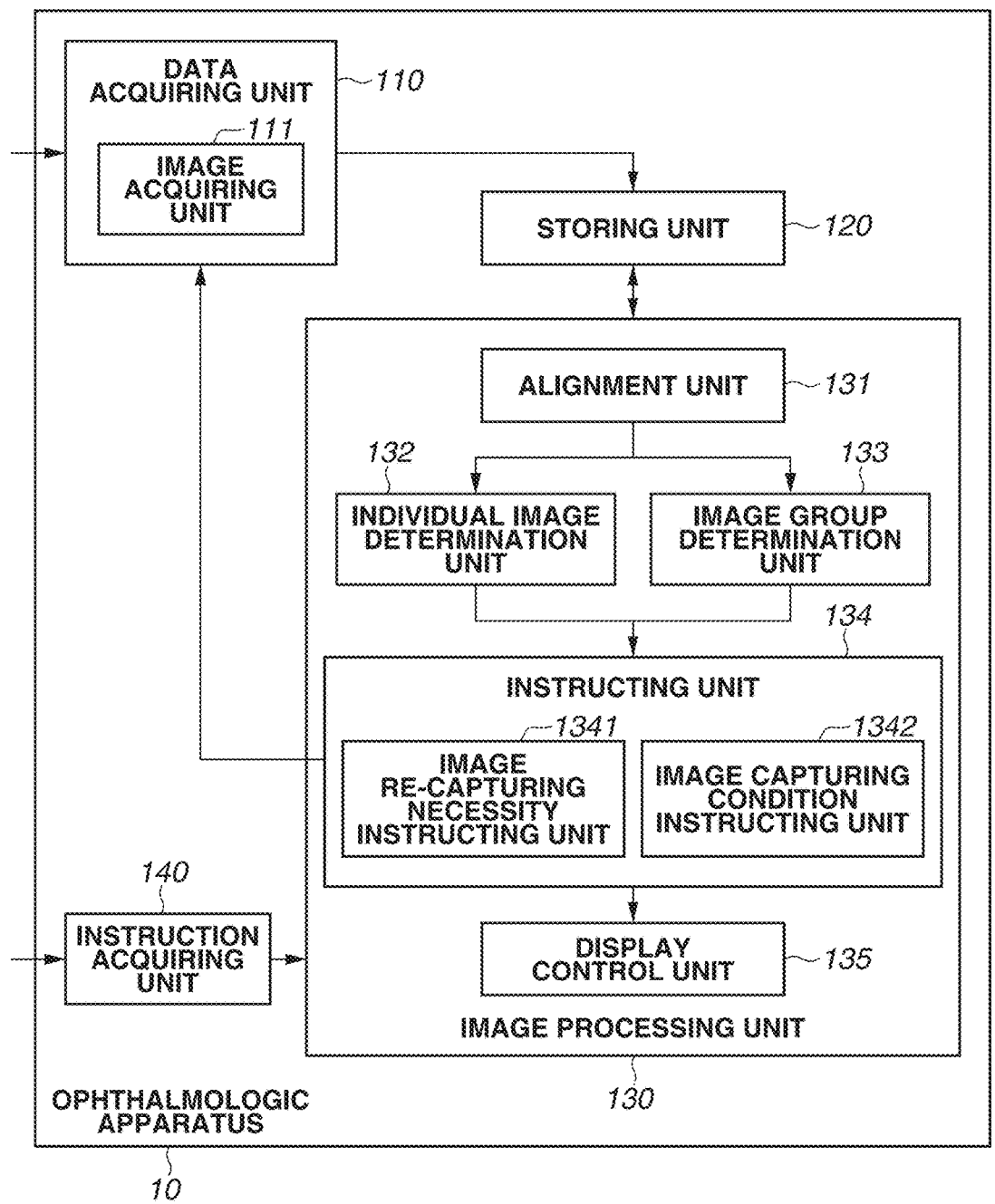
FIG. 9 is a block diagram illustrating a functional configuration of an ophthalmologic apparatus according to a third exemplary embodiment of the present invention.
Figure 11A:
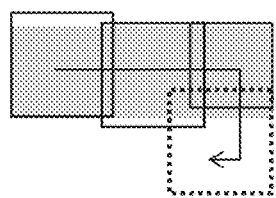
FIGS. 11A, 11B, 11C, 11D, and 11E illustrate the contents of image processing according to the third exemplary embodiment of the present invention.
Figure 11B:
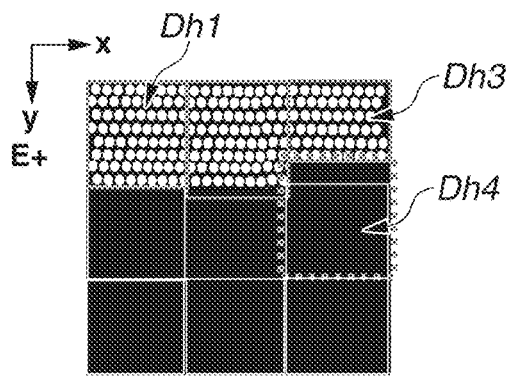

A third exemplary embodiment will be described in detail below. An ophthalmologic apparatus according to the third exemplary embodiment is different from the ophthalmologic apparatus according to the first exemplary embodiment characterized by determining the image group conformity after acquiring all images constituting an image group corresponding to a single fixation position. The ophthalmologic apparatus according to the third exemplary embodiment determines the image group conformity every time an individual image is acquired. The ophthalmologic apparatus according to the third exemplary embodiment is configured to give an instruction on image capturing conditions for the next image based on an image group conformity determination result, so that the conformity tends to become higher. Specifically, it is now assumed that an image group to be acquired is composed of nine high magnification images as illustrated in FIG. 11B. In this case, the ophthalmologic apparatus gives an instruction on an acquisition position for the next image (i.e., the fourth image) based on an acquisition region of three images having been already captured in such a way as to eliminate any image missing region, as described in detail below. The configuration of each device connected to an ophthalmologic apparatus 10 according to the present exemplary embodiment is similar to that described in the first exemplary embodiment and therefore redundant description thereof will be avoided. FIG. 9 is a diagram illustrating functional blocks of the ophthalmologic apparatus 10 according to the present exemplary embodiment. The ophthalmologic apparatus 10 according to the present exemplary embodiment is different from that described in the first exemplary embodiment in that the instructing unit 134 includes an image capturing condition instructing unit 1342. FIG. 10 illustrates an image processing flow according to the present exemplary embodiment. Processing to be performed in step S1010, step S1020, step S1030, step S1040, step S1045, step S1075, step S1080, and step S1085 is similar to the processing performed in step S510, step S520, step S530, step S540, step S545, step S575, step S580, and step S585 in the first exemplary embodiment. Therefore, in the present exemplary embodiment, processing to be performed in step S1050, step S1060, step S1065, and step S1070 will be described in detail below. However, in the present exemplary embodiment, the processing to be performed in step S1020 and step S1030 (i.e., image acquisition and image alignment) is not applied to all of the high magnification images. The ophthalmologic apparatus 10 performs the image alignment processing using only currently acquired images each time when the image acquisition processing for a single image is completed.

<Step S1050: Display>

The display control unit 135 forms a matrix-like composite composed of the individual images having been formed based on the alignment parameter obtained in step S1030 and causes the monitor 305 to display the group of composite images. Through the above-mentioned processing, image capturing results can be sequentially confirmed.

<Step S1060: Image Group Conformity Determination Processing>

The image group determination unit 133 determines the conformity based on the relative position and the continuity in luminance characteristics of a group of high magnification images currently acquired, in the imaging target region. In the present exemplary embodiment, the image group is composed of three high magnification images Dhj (Dh1 to Dh3) having been already acquired as illustrated in FIG. 11A. The image number j is initially set on an upper left image. The image number j increments successively according to the raster scanning (i.e., zigzag scanning) order. According to the example illustrated in FIG. 11A, the third image Dh3 includes an image missing region as apparent when the imaging target regions (i.e., gray regions) of the images Dh1 to Dh3 are compared with one another. Therefore, the image group determination unit 133 calculates the image group conformity according to the following formula.

$$\text{(Number of currently acquired images–Number of images including any image missing region)/ (Number of currently acquired images)} \quad \text{Formula:}$$

Then, the image group determination unit 133 stores the image number j of the image containing the image missing region, in the storing unit 120. However, the image group conformity is not limited to the above-mentioned example. Any other arbitrary index can be set if it is available to determine the image group conformity. In this case, the display control unit 135 can cause the monitor 305 to perform an arbitrary discriminable display (e.g., putting a color frame to a corresponding image region) for the image including the image missing region determined by the image group determination unit 133.

<Step S1065: Determining Whether the Image Group has been Entirely Obtained>

The ophthalmologic apparatus 10 determines whether the image group of the image acquisition pattern acquired in step S510 has been entirely obtained. If it is determined that the image group has been entirely obtained (YES in step S1065), the operation proceeds to step S1075. If it is determined that there is any image that has not yet been obtained (NO in step S1065), the operation proceeds to step S1070.

<Step S1070: Instruction on Image Capturing Conditions for an Image to be Acquired Next>

The image capturing condition instructing unit 1342 instructs the image acquiring unit 111 to set image capturing conditions for the high magnification image (Dh4) to be acquired next in such a way as to increase the determined image group conformity to a maximum value (namely, 1 in the present exemplary embodiment). Then, the operation proceeds to step S1020. For example, it is now assumed that the high magnification images Dh1 to Dh3 have been already acquired and the third image Dh3 includes an image missing region at the lower edge thereof as illustrated in FIG. 11B. In this case, the instructing unit 134 instructs the image acquiring unit 111 to change the photographing center (i.e., a part of the image capturing conditions for the next image Dh4) in the following manner.

(i) The instruction includes moving an image pickup center upward within the range capable of eliminating the image missing region in such a manner that the moving distance can be minimized. The image capturing condition setting (changing) method is not limited to the above-mentioned example. The image capturing conditions can be arbitrarily changed.

(ii) For example, the instruction includes widening the angle of view within the range capable of eliminating the image missing region in such a manner that the change amount of the angle of view can be minimized.

Figure 11C:
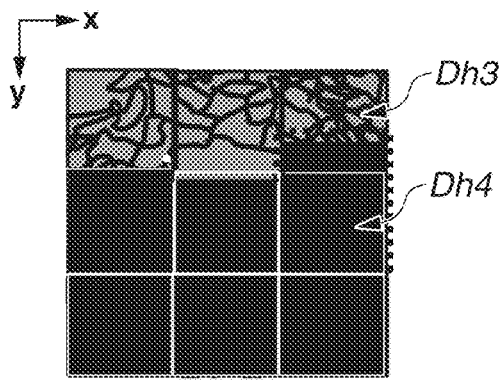
Figure 11D:
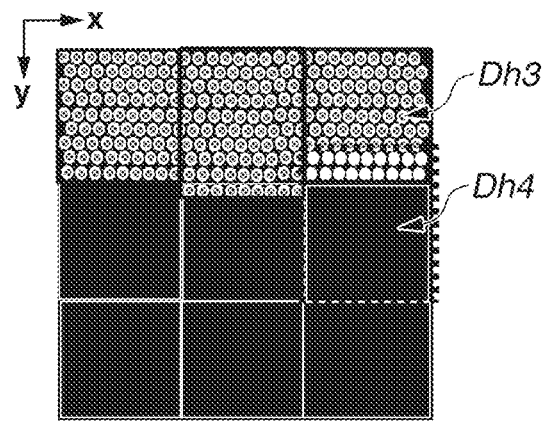
Figure 11E:
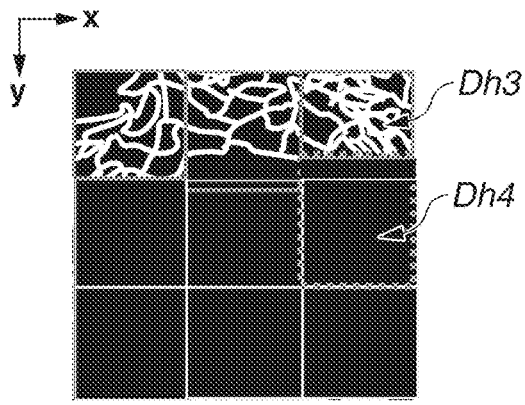

The instruction can be a combination of the above-mentioned contents. In the present exemplary embodiment, the imaging target is visual cells and the imaging target region includes an image missing part. However, the present invention is not limited to the above-mentioned example. For example, in a case where a capillary is photographed as another imaging target, the image capturing conditions for the next image can be similarly set (see FIG. 11C). In the present exemplary embodiment, the ophthalmologic apparatus determines the image group conformity based on the presence of any image missing part in the imaging target region (i.e., the continuity of luminance characteristics). However, the present invention is not limited to the above-mentioned example. Similar to the second exemplary embodiment, the ophthalmologic apparatus 10 can be configured to include the image feature acquiring unit 1321 in the individual image determination unit 132 to determine the image group conformity based on the image feature continuity extracted from neighboring high magnification images and give an instruction on the image capturing conditions for the next image (see FIGS. 11D and 11E).

According to the above-mentioned configuration, the ophthalmologic apparatus 10 determines the image group conformity after acquiring each image and instructs the image capturing conditions for the next image in such a way as to satisfy the criteria of the image group conformity. Through the above-mentioned processing, in a case where an observation or analysis target cell group (or tissue) and a lesion thereof extend beyond the acquisition positions of a plurality of high magnification images, it becomes feasible to capture a group of observable or analyzable images under substantially the same conditions.

[Tomographic Image Capturing Apparatus Including an Adaptive Optical System]

A fourth exemplary embodiment will be described in detail below. In displaying a composite of high-magnification adaptive optics OCT tomographic images captured at different photographing positions, an ophthalmologic apparatus according to the present exemplary embodiment determines the image group conformity based on the smallness of a non-observable (unanalyzable) region in comparison with a photographing (analysis) target region. Specifically, the ophthalmologic apparatus according to the present exemplary embodiment acquires a plurality (3×3×3=27) of high magnification images that constitute a cubic shape in the vicinity of the fovea centralis. Then, in forming an image composite through alignment processing, the ophthalmologic apparatus determines the smallness of a non-observable (unanalyzable) region in comparison with the image pickup (analysis) target region, as the image group conformity, as described in detail below.

Figure 2C:
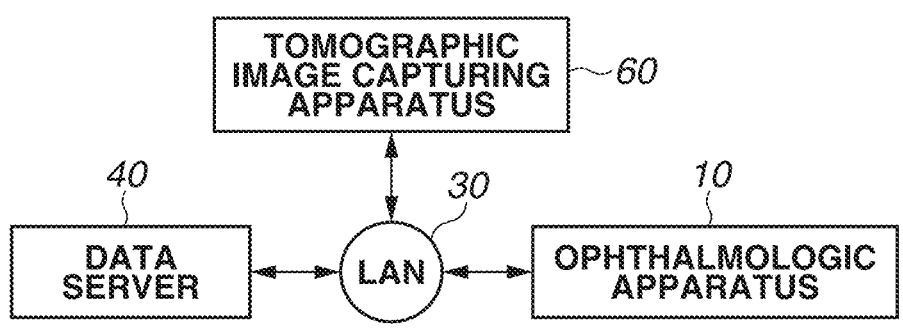

FIG. 2C illustrates a configuration of peripheral devices connected to an ophthalmologic apparatus 10 according to the present exemplary embodiment. The present exemplary embodiment is different from the first exemplary embodiment in that the ophthalmologic apparatus 10 is connected to a tomographic image capturing apparatus 60 including an adaptive optical system. The tomographic image capturing apparatus 60 can capture a tomographic image of an eye. For example, the tomographic image capturing apparatus 60 is a spectral domain optical coherence tomography (SD-OCT) apparatus. The tomographic image capturing apparatus 60 can capture tomographic images of an examinee's eye three-dimensionally according to an operation of an operator (not illustrated). The tomographic image capturing apparatus 60 transmits the captured tomographic images to the ophthalmologic apparatus 10. Functional blocks of the ophthalmologic apparatus 10 according to the present exemplary embodiment are similar to those described in the first exemplary embodiment and therefore redundant description thereof will be avoided. Further, the data server 40 can store normal value data representing eye image features and distributions thereof. More specifically, in the present exemplary embodiment, the data server 40 stores normal value data relating to the retina layer boundary and the shape/thickness thereof.

Figure 12:
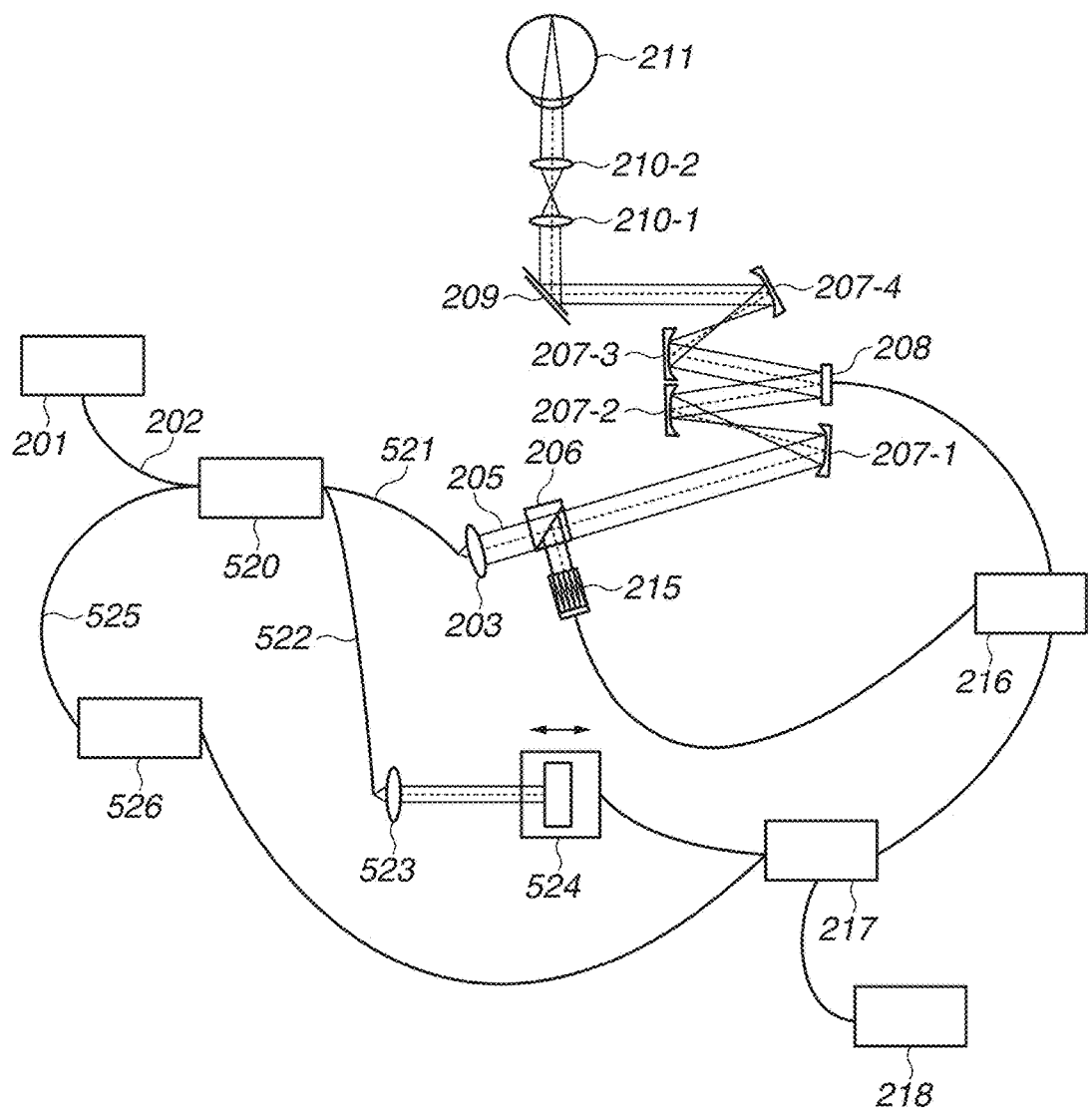
FIG. 12 illustrates an entire configuration of a tomographic image capturing apparatus according to a fourth exemplary embodiment of the present invention.

FIG. 12 illustrates a configuration of the tomographic image capturing apparatus 60 including the adaptive optical system. In FIG. 12, the light source 201 is an SLD light source having a wavelength of 840 nm. It is desired that the light source 201 is a low-coherence type. For example, it is desired that the wavelength width of the SLD light source is equal to or greater than 30 nm. For example, a titanium-sapphire laser or any other appropriate ultrashort pulse laser can be used as the light source. The light emitted from the light source 201 reaches a fiber coupler 520 via the single-mode optical fiber 202. The fiber coupler 520 separates the light path into a measurement light path 521 and a reference light path 522. The branching ratio of the fiber coupler 520 is set to be 10:90 so that 10% of the input light can be guided into the measurement light path 521. The light having passed through the measurement light path 521 reaches the collimator 203. The light travels as parallel measurement light from the collimator 203. The rest of the tomographic image capturing apparatus 60 is similar to that described in the first exemplary embodiment. The eye 211 is irradiated with light having passed through the adaptive optical system and the scanning optical system. The light reflected or scattered from the eye 211 travels in an opposite direction along a path similar to the above-mentioned path and reaches the fiber coupler 520 again via the optical fiber 521. On the other hand, the reference light having passed through the reference light path 522 reaches a collimator 523. The light having passed through the collimator 523 travels toward a light-path-length changing unit 524. The light reflected by light-path-length changing unit 524 reaches the fiber coupler 520 again. The measurement light and the reference light having reached the fiber coupler 520 are then multiplexed and guided into a spectroscope 526 via an optical fiber 525. The control unit 217 can form a tomographic image of the eye based on information about interference light dispersed by the spectroscope 526. The control unit 217 can control the light-path-length changing unit 524 to acquire a tomographic image at a desired depth position. If the scanning optical system illustrated in FIG. 12 is configured to have an increased swing angle and the adaptive optics control unit 216 is prevented from performing the aberration correction, the tomographic image capturing apparatus 60 can operate as an ordinary tomographic image capturing apparatus and can capture a wide viewing angle tomographic image (i.e., the wide viewing angle image Dl).

Further, in the present exemplary embodiment, the tomographic image capturing apparatus 60 including the adaptive optical system uses the SD-OCT. However, the tomographic image capturing apparatus 60 is not limited to the SD-OCT apparatus. For example, the tomographic image capturing apparatus 60 can be configured as a time-domain OCT apparatus or a swept source optical coherence tomography (SS-OCT) apparatus. The SS-OCT apparatus uses a light source capable of emitting light of different wavelengths at different times. Therefore, it is unnecessary to provide a spectroscopic element that acquires spectral information. Further, the SS-OCT apparatus can acquire a deep reaching depth image that can include not only a retina but also a choroid. FIG. 5 illustrates an image processing flow that can be performed by the ophthalmologic apparatus 10 according to the present exemplary embodiment. Processing to be performed in step S550, step S565, step S575, step S580, and step S585 is similar to the processing described in the first exemplary embodiment and redundant description thereof will be avoided.

<Step S510: Image Acquisition Pattern Selection>

Figure 13A:
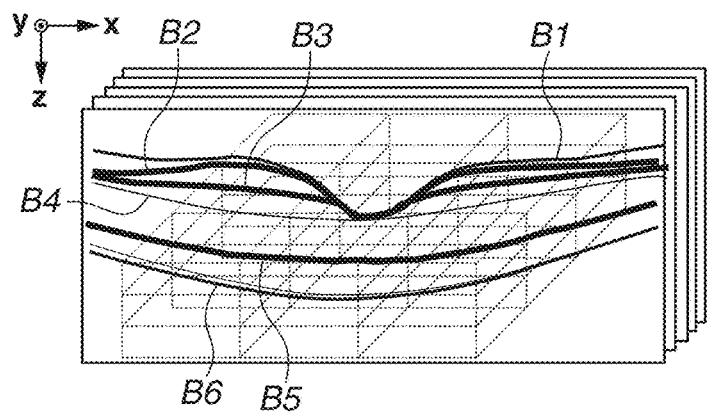
FIGS. 13A, 13B, 13C, and 13D illustrate the contents of image processing according to the fourth exemplary embodiment of the present invention.
Figure 13B:
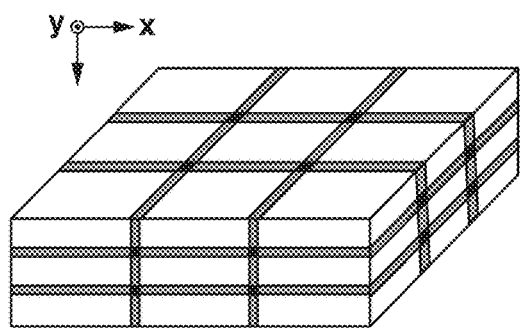
Figure 13C:
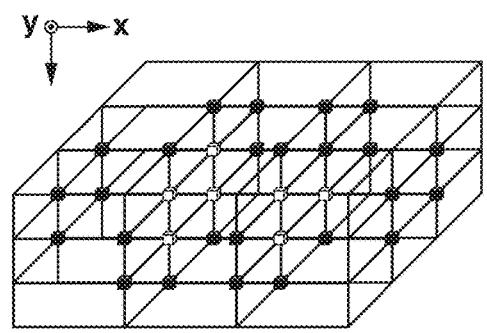

The ophthalmologic apparatus 10 acquires information about a predetermined image acquisition pattern (e.g. photographing position or angle of view) having been selected by a user, via the instruction acquiring unit 140. In the present exemplary embodiment, the ophthalmologic apparatus 10 sets the fixation target positions Fl and Fh to a fovea centralis of a macula and acquires the wide viewing angle image Dl and the high magnification images Dhj illustrated in FIG. 13A. More specifically, the ophthalmologic apparatus 10 acquires a plurality (3×3×3=27) of high magnification images that constitute a cubic shape in the vicinity of the fovea centralis. In this case, the display contents do not include any overlapping region between high-magnification images because the purpose of the display is indicating the photographing position explicitly. In actuality, the photographing position, the angle of view, and the number of slices are set in such a manner that an overlapping region exists between high-magnification images as illustrated in FIG. 13B. In FIG. 13B, a gray region indicates an overlapping region between two neighboring images, and a black region indicates an overlapping region between four neighboring images. In FIG. 13C, a white lattice point indicates an overlapping region between eight neighboring images. The photographing position setting method is not limited to the above-mentioned example. The photographing position can be set to an arbitrary position.

<Step S520: Image Acquisition>

The image acquiring unit 111 requests the tomographic image capturing apparatus 60 to acquire wide viewing angle image Dl and high magnification images Dhj, and corresponding fixation target positions Fl and Fh, based on the information about the image acquisition pattern designated in step S510. In the present exemplary embodiment, the image acquiring unit 111 sets the fixation target positions Fl and Fh to a fovea centralis of a macula and acquires the wide viewing angle image Dl and the high magnification images Dhj. The photographing position setting method is not limited to the above-mentioned example. Each of the fixation target positions Fl and Fh can be set to an arbitrary position.

In response to the acquisition request, the tomographic image capturing apparatus 60 acquires and transmits the wide viewing angle image Dl, the high magnification images Dhj, and the corresponding fixation target positions Fl and Fh. The image acquiring unit 111 receives the wide viewing angle image Dl, the high magnification images Dhj, and the corresponding fixation target positions Fl and Fh from the tomographic image capturing apparatus 60 via the LAN 30. The image acquiring unit 111 stores the received data in the storing unit 120. In the present exemplary embodiment, the wide viewing angle image Dl and the high magnification images Dhj are three-dimensional images having been already subjected to inter-slice alignment.

<Step S530: Alignment>

The alignment unit 131 determines the alignment of the high magnification images Dhj relative to the wide viewing angle image Dl and obtains the position of each high magnification image Dhj on the wide viewing angle image Dl. First, the alignment unit 131 acquires the fixation target position Fh used in a photographing operation to acquire the high magnification images Dhj from the storing unit 120. Then, the alignment unit 131 sets an initial search point of the alignment parameter in the alignment between the wide viewing angle image Dl and the high magnification images Dhj based on a relative distance from the acquired fixation target position. If there is any overlapping region between the high magnification images Dhj, the alignment unit 131 calculates an inter-image similarity with respect to the overlapping region. Then, the alignment unit 131 aligns the positions of respective high magnification images Dhj in such a way as to maximize the inter-image similarity.

Next, in a case where the images acquired in step S530 include two or more images that are mutually different in magnification, the alignment unit 131 prioritizes the alignment of a lower magnification image. In the present exemplary embodiment, the images acquired in step S530 are high magnification images only. Therefore, the alignment unit 131 determines the alignment of the high magnification images Dhj relative to the wide viewing angle image Dl. Further, any other conventionally known methods can be used arbitrarily in checking the inter-image similarity or performing the coordinate conversion. In the present exemplary embodiment, the inter-image similarity used, in determining the alignment is a three-dimensional correlation coefficient. The coordinate conversion method used in determining the alignment is three-dimensional Affine conversion.

<Step S540: Conformity Determination Processing Performed for Each of Images at Different Positions>

The individual image determination unit 132 performs conformity determination processing based on a luminance value of each slice or an inter-slice movement amount. In this case, the processing for acquiring the determination criteria and the method for determining the conformity are basically similar to those described in the first exemplary embodiment (see step S540). In the present exemplary embodiment, the last two determination criteria are as follows.

c) The movement amount between slices is within an adequate range.

d) The coherence gate is within an adequate range.

In this case, the individual image determination unit 132 determines the total number of obtained slices not including any low-luminance slice that may be caused due to nictation, as the conformity. Further, in a case where the conformity satisfies the predetermined criteria, the image processing unit 130 forms an individual image. In the present exemplary embodiment, the high magnification images are three-dimensional images obtained by photographing visual cells. If there is any slice that cannot satisfy the criterion a), the individual image determination unit 132 can calculate a pixel value of such a defective slice through interpolation processing applied to the pixel values of a preceding slice and a following slice. Further, if a slice whose pixel value at each pixel position is less than a predetermined value (e.g., 0) is included, a pixel value of a corresponding portion (i.e., an image edge portion) is set to 0. Accordingly, in a case where an image has a large value in fixation disparity (i.e., a large inter-slice movement amount), the pixel value becomes 0 in a larger image edge region.

<Step S545: Image Re-Capturing Necessity Instruction>

The image re-capturing necessity instructing unit 1341 instructs the image acquiring unit 111 about the necessity of re-capturing the corresponding high magnification image Dhj based on the individual image conformity determined in step S540. Specifically, in a case where the individual image conformity does not satisfy the predetermined criteria, the image re-capturing necessity instructing unit 1341 determines that the image re-capturing processing is necessary because the number of observable slices does not satisfy a threshold value Tf (YES in step S545). Thus, the image re-capturing necessity instructing unit 1341 instructs the image acquiring unit 111 to re-capture a corresponding image. The operation returns to step S520. If the individual image conformity satisfies the predetermined criteria (NO in step S545), the operation proceeds to step S550.

<Step S560: Processing for Determining the Image Group Conformity>

The image group determination unit 133 forms a matrix-like composite composed of the images formed in step S540 based on the alignment parameter obtained in step S530, and determines the conformity based on the relative position and the luminance continuity of the image group. If the image group conformity does not satisfy the predetermined criteria, the instructing unit 134 instructs the image acquiring unit 111 to re-capture a corresponding image. In the present exemplary embodiment, the image number j is initially set on an upper left image. The image number j increments successively according to the raster scanning (i.e., zigzag scanning) order. The following is a determination policy with respect to the conformity of the image composite (i.e., the image group), more specifically, the image group conformity required to observe the entire image composite under the same conditions.
1. The image composite does not include any image missing region (in other words, the luminance does not change discontinuously).
2. The image quality is stable irrespective of photographing positions.

In this case, if the necessity of performing the image re-capturing processing is determined based on only the conformity of an individual image, instead of determining the image group conformity, strictly determining whether an imaging target region has been acquired will be necessary for each image. As a result, the instruction to re-capture an image will be frequently given. In this case, it will be necessary to set a wider overlapping region (i.e., increase the number of image pickup positions or widen the angle of view) to prevent the image re-capturing determination from increasing.

Therefore, in the present exemplary embodiment, The continuity or the subsidiarity of data at an edge portion or an overlapping region between neighboring images is taken into consideration in determining the conformity so that a group of high magnification images satisfying the condition 1 can be efficiently acquired. Specifically, in the present exemplary embodiment, there is an overlapped region between two neighboring images (i.e., a gray region illustrated in FIG. 13B) or between four neighboring images (i.e., a black region illustrated in FIG. 13B). Further, there is an overlapped region between eight neighboring images (as indicated by white lattice points in FIG. 13C). Even in a case where a single image includes an image missing region, if there is any data obtainable from the overlapped region between neighboring images, it is determined that the image group does not include any image missing region. Therefore, the image group conformity can be determined according to the following procedure. More specifically, the image group conformity determination procedure includes:

(1) forming a matrix-like composite composed of the individual images generated in step S540 according to the alignment parameter obtained in step S530;
(2) completing the formation of the image composite immediately if there is not any image missing region; and
(3) identifying the position of each image missing region if the image missing region is present, and obtaining a number list of the image to which the image missing region belongs.

Figure 13D:
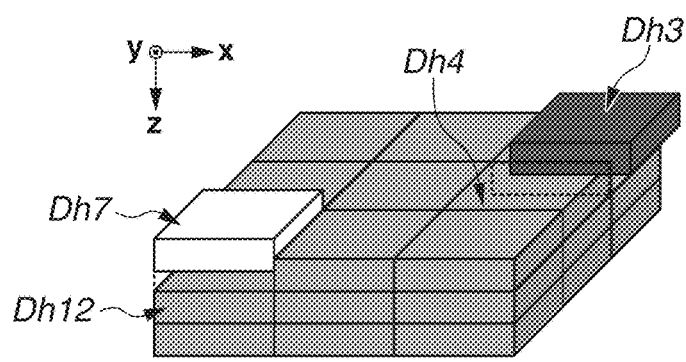

For example, according to the example illustrated in FIG. 13D, each of the high magnification images Dh3 and Dh7 includes an image missing region that has been caused by the composite processing. Therefore, the image group determination unit 133 obtains a number list of the image including the image missing region.

(4) The image group determination unit 133 calculates the image group conformity according to the following formula.

Formula:
(Total number of composite images−number of images including any image missing region)/ (Total number of composite images)

The formula defining the image group conformity is not limited to the above-mentioned example. For example, the following formula can be used.

Formula:
(Volume(number of pixels) of an logical sum (OR) region in the imaging target region−Volume (number of pixels) of the image missing region)/(Volume (number of pixels) of the OR region in the imaging target region)

Alternatively, the following formula can be used in a case where a composite of projection images of individual images is formed on a projection image of the wide viewing angle image based on the alignment parameter obtained in step S520.

Formula:
(Area of the OR region in the imaging target region−Area of the image missing region)/(Area of the OR region in the imaging target region)

The image group conformity determination policy is not limited to the above-mentioned example. Any other conformity can be arbitrarily set. For example, in addition to the number of pixels or areas, it is useful that the length of the non-blood vessel region boundary (i.e., an example of the image feature) is included as a part of the conformity conditions.

<Step S570: Display>

The display control unit 135 causes the monitor 305 to display the image composite formed in step S560. In the present exemplary embodiment, the wide viewing angle image Dl and the high magnification images Dhj are three-dimensional tomographic images. Therefore, the display processing to be performed by the display control unit 135 is the following two types.

i) The display control unit 135 generates projection images of the wide viewing angle image Dl and the high magnification images Dhj in the z-axis direction and displays a composite of the projection images of the high magnification images Dhj superimposed on the projection image of the wide viewing angle image Dl.

ii) The display control unit 135 generates a three-dimensional wide viewing angle tomographic image Dl" that can be displayed with a pixel value of the three-dimensional wide viewing angle tomographic image Dl at a position where only the three-dimensional wide viewing angle tomographic image Dl has been acquired and a pixel value of the three-dimensional high-magnification tomographic image Dhj at a position where both of the three-dimensional wide viewing angle tomographic image Dl and the three-dimensional high-magnification tomographic image Dhj have been acquired. Further, the display control unit 135 displays, on the superimposing image obtained through the above-mentioned processing i), an arrow indicating a specific scanning position on the three-dimensional wide viewing angle tomographic image Dl" and obtains a two-dimensional tomographic image of the three-dimensional wide viewing angle tomographic image Dl" that has been taken at the arrow position. Then, the display control unit 135 causes the monitor 305 to display the obtained two-dimensional tomographic image in parallel with the superimposing image obtained through the above-mentioned processing i). The above-mentioned display includes not only superimposing a two-dimensional tomographic image of the three-dimensional wide viewing angle tomographic image Dl but also superimposing a two-dimensional tomographic image of the three-dimensional high-magnification tomographic image Dhj. Further, in the above-mentioned display processing ii), an operator can move the arrow indicating the display position of the wide viewing angle tomographic image Dl" (in the up-and-down direction or in the right-and-left direction) via the instruction acquiring unit 140. Therefore, it is feasible to change the display slices of the wide viewing angle image Dl and the high magnification images Dhj to be taken (displayed) according to the operation.

Further, in a case where the acquired images include a plurality of high magnification images Dhj captured at different photographing positions as described in the present exemplary embodiment, the display control unit 135 performs display gradational conversion processing on respective high magnification images Dhj. Further, in a case where the photographing positions of two high magnification images Dhj are closely located (or when the photographing positions are the same), any one of the following methods can be used to display an overlapping region. More specifically, according to a first display method, the display control unit 135 calculates a quality index value of each image beforehand and causes the monitor 305 to display an image that is largest in evaluation value. According to a second display method, the display control unit 135 performs blending of the luminance of respective high magnification images Dhj (weighting the degree of transparency based on the above-mentioned quality index value of each image). The image quality index to be used in this case can be an arbitrary index that is conventionally known. In the present exemplary embodiment, the quality index value is an average luminance value of the image histogram. The method for generating the above-mentioned projection images is not limited to the average value projection. Any other projection method can be arbitrarily used. Further, the high magnification images Dhj are not limited to still images and can be moving images.

In the present exemplary embodiment, the display of high magnification images on the monitor 305 does not start before completing the acquisition of all images. However, the present invention is not limited to the above-mentioned example. For example, the display control unit 135 can be configured to cause the monitor 305 to display a formed image and/or a result of the individual image conformity determination, so that image capturing results can be sequentially confirmed. In this case, if there is an image that is determined as being low in conformity and requiring the image re-capturing processing, the display control unit 135 can cause the monitor 305 to perform an arbitrary discriminable display (e.g., giving color to a corresponding image pickup region or a frame thereof). As mentioned above, in the present exemplary embodiment, the ophthalmologic apparatus 10 determines the tomographic image group conformity based on the smallness of a non-observable region relative to the imaging target region. However, the present invention is not limited to the above-mentioned example. Similar to the second exemplary embodiment, the ophthalmologic apparatus 10 can be configured to include the image feature acquiring unit 1321 in the individual image determination unit 132, so that the tomographic image group conformity can be determined based on the continuity of the image features extracted from respective high magnification images, between neighboring images. For example, the image feature acquiring unit 1321 extracts a layer boundary (e.g., inner boundary film B1, nerve fiber layer boundary B2, inner plexiform layer boundary B4, visual cell inner and outer segments boundary B5, or retinal pigment epithelium boundary B6) as the image feature though the following procedure and determines the tomographic image group conformity based on the continuity of each layer boundary position.

A feature extraction procedure for the wide viewing angle image Dl will be described in detail below. First, a procedure for extracting a layer boundary will be described in detail below. In this case, it is assumed that a processing target three-dimensional tomographic image is a composite composed of two-dimensional tomographic images (B scan images). The image feature acquiring unit 1321 performs the following processing for each two-dimensional tomographic image. First, the image feature acquiring unit 1321 performs smoothing processing on a target two-dimensional tomographic image to remove noise components. Next, the image feature acquiring unit 1321 detects edge components from the two-dimensional tomographic image and extracts some line segments as layer boundary candidates based on the connectivity thereof. Then, the image feature acquiring unit 1321 extracts, from the extracted candidates, the uppermost line segment as the inner boundary film B1, the second uppermost line segment as the nerve fiber layer boundary B2, and the third uppermost line segment as the inner plexiform layer boundary B4. Further, the image feature acquiring unit 1321 extracts a line segment having a maximum contrast positioned on the outer layer side of the inner boundary film B1 (i.e., a high-value side of the z coordinate in FIG. 6A) as the visual cell inner and outer segments boundary B5. Further, the image feature acquiring unit 1321 extracts the lowermost line segment from the layer boundary candidate group as the retinal pigment epithelium boundary B6. Further, the apparatus can be configured to perform precise extraction by applying the variable shape model (e.g., Snakes or level set method) while setting these line segments as initial values. Further, the apparatus can be configured to extract each layer boundary according to the graph cut method. The boundary extraction using the variable shape model or the graph cut method can be applied to the three-dimensional tomographic image three-dimensionally or can be applied to respective two-dimensional tomographic images two-dimensionally. Further, the layer boundary extraction method can be any other method if it can extract a layer boundary from a tomographic image of an eye. Further, extracting a layer boundary from respective high magnification images Dhj can be performed based on the relative position between the wide viewing angle image Dl and respective high magnification images Dhj and the layer boundary position detected from the wide viewing angle image Dl. More specifically, the layer boundary extraction can be performed by detecting the boundary of a corresponding layer on the high magnification image Dhj in the vicinity of each layer boundary position, detected from the wide viewing angle image Dl associated with respective high magnification images Dhj.

According to the above-mentioned configuration, in displaying a composite of high-magnification adaptive optics OCT tomographic images captured at different photographing positions, the ophthalmologic apparatus 10 determines the image group conformity based on the smallness of a non-observable (unanalyzable) region in the image composite in comparison with the photographing (analysis) target region. Through the above-mentioned processing, in a case where an observation or analysis target cell group (or tissue) and a lesion thereof extend beyond the acquisition positions of a plurality of high magnification images, it becomes feasible to capture a group of observable or analyzable images under substantially the same conditions.

[Comparing an Image Composite with Regions Having been Imaged (or Analyzed) in a Different Examination]

A fifth exemplary embodiment will be described in detail below. In displaying a composite of high-magnification adaptive optics SLO images captured at different photographing positions, an ophthalmologic apparatus according to the present exemplary embodiment is characterized by determining the image group conformity based on the smallness of a non-observable (unanalyzable) region in comparison with the regions having been imaged (or analyzed) in a different examination. Specifically, the ophthalmologic apparatus determines the image group conformity based on the smallness of a non-observable (unanalyzable) region in comparison with an image group Dhjf (f=1, 2, ..., and n−1) captured at past examination date and time, as described in detail below.

Figure 14:
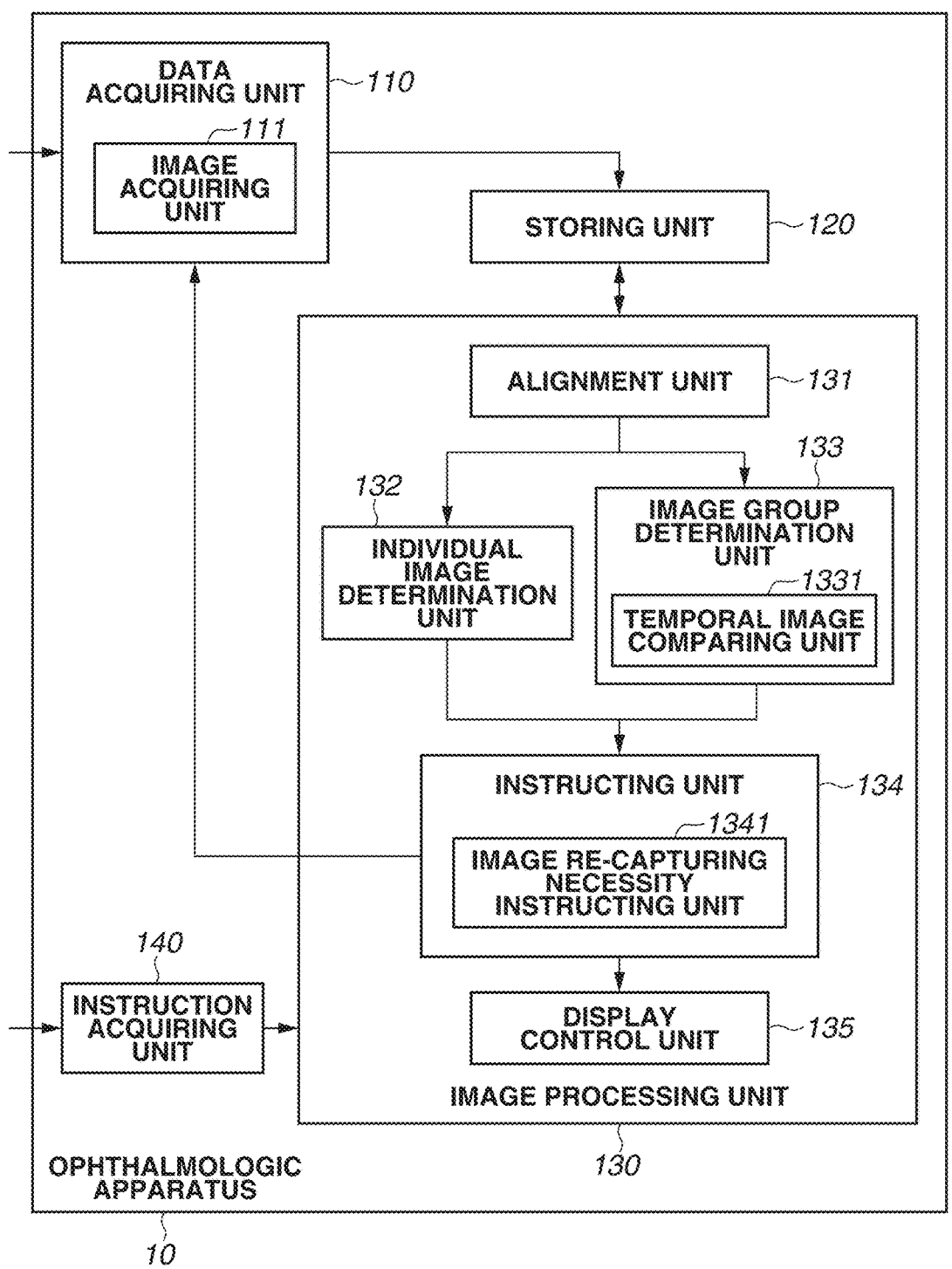
FIG. 14 is a block diagram illustrating a functional configuration of an ophthalmologic apparatus according to the fifth exemplary embodiment of the present invention.

The configuration of each device connected to an ophthalmologic apparatus 10 according to the present exemplary embodiment is similar to that described in the first exemplary embodiment. FIG. 14 is a diagram illustrating functional blocks of the ophthalmologic apparatus 10 according to the present exemplary embodiment. The ophthalmologic apparatus 10 illustrated in FIG. 14 is different from that described in the first exemplary embodiment in that the image group determination unit 133 includes a temporal image comparing unit 1331. Further, an image processing flow according to the present exemplary embodiment is similar to that illustrated in FIG. 5. Processing to be performed in respective steps, except for step S510, step S520, step S530, step S560, and step S570 is similar to that described in the first exemplary embodiment. Therefore, in the present exemplary embodiment, processing to be performed in step S510, step S520, step S530, step S560, and step S570 will be described in detail below. In the following description, Dsjf and Fsf represent SLO images and fixation target positions when there is a plurality of acquired images that are different from each other in magnification, photographing position, and examination date and time. More specifically, the suffix "s" (s=1, 2, ..., and smax) is a variable representing the magnification. The suffix "j" (j=1, 2, ..., and jmax) is a variable representing the photographing position number. The suffix "f" (f=1, 2, ..., and fmax) is a variable representing the examination date and time. In this case, when the variable "s" decreases, the photographing magnification becomes larger (namely, the angle of view becomes narrower). When the variable "f" is smaller, the examination date and time is older. In the present exemplary embodiment, there is only one photographing position that corresponds to the lowest magnification image (i.e., the wide viewing angle image) and therefore no photographing position number thereof is allocated.

<Step S510: Image Acquisition Pattern Selection>

The ophthalmologic apparatus 10 acquires information about a predetermined image acquisition pattern (e.g., photographing position or angle of view) having been selected by a user, via the instruction acquiring unit 140. In the present exemplary embodiment, the ophthalmologic apparatus 10 sets the fixation target positions F2 and F1 to a fovea centralis of a macula and acquires a wide viewing angle image D2 and the high magnification image D1j illustrated in FIG. 6H. The photographing position setting method is not limited to the above-mentioned example. The photographing position can be set to an arbitrary position.

<Step S520: Image Acquisition>

The image acquiring unit 111 requests the data server 40 to transfer past SLO images Dsjf (f=1, 2, ..., and n−1) of the same examinee's eye which have been captured using the image acquisition pattern designated in step S510, together with the fixation target position Fsf and the alignment parameter value corresponding to the SLO image Dsjf. The data server 40 transfers data corresponding to the request to the ophthalmologic apparatus 10. The ophthalmologic apparatus 10 stores the acquired data in the storing unit 120. In the present exemplary embodiment, n is set to 4 (n=4).

Next, the image acquiring unit 111 requests the SLO image capturing apparatus 20 to acquire the latest examination image and corresponding fixation target positions, more specifically, SLO image Dsjn and fixation target position Fsn.

<Step S530: Alignment>

The alignment unit 131 determines the alignment of high magnification images D1jf relative to a wide viewing angle image D2f (f=1, 2, ..., and n) and obtains the relative position of each high magnification image D1jf on the wide viewing angle image D2f, thereby generating an image composite composed of the images D1jf. If there is any overlapping region between the high magnification images D1jf captured on the same examination date, the alignment unit 131 calculates an inter-image similarity of the overlapping region. Then, the alignment unit 131 aligns the positions of respective high magnification image D1jf in such a way as to maximize the inter-image similarity. In a case where the acquired images include three or more images that are mutually different in magnification, the alignment unit 131 prioritizes the alignment of a lower magnification image. For example, in a case where the acquired images are an image D3f, an image D2kf, and the image D1jf, the alignment unit 131 first determines the alignment between the image D3f and the image D2kf. Next, the alignment unit 131 determines the alignment between the image D2kf and the image D1jf. Further, the alignment unit 131 acquires the fixation target position F1f used in a photographing operation to acquire the image D1jf from the storing unit 120. Then, the alignment unit 131 sets an initial search point of the alignment parameter in the alignment between the image D2f and the image D1jf based on a relative distance from the acquired position. Further, any other conventionally known methods can be arbitrarily used in checking the inter-image similarity or performing the coordinate conversion. The inter-image similarity used in the present exemplary embodiment is a correlation coefficient. The coordinate conversion method used to determine the alignment is Affine conversion.

Next, the alignment unit 131 determines the alignment between the wide viewing angle image D2n in the latest examination and the wide viewing angle image D2f (f=1, 2, ..., and n−1) in the past examination. Further, the alignment unit 131 obtains the relative position of the high magnification image D1jf in the past examination relative to the high magnification image D1jn in the latest examination, with reference to the relative position of the wide viewing angle image D2n relative to the high magnification image D1jn, the relative position of the wide viewing angle image D2f relative to the wide viewing angle image D2n, and the relative position of the high magnification image D1jf relative to the wide viewing angle image D2f. Alternatively, the alignment unit 131 can directly determine the alignment between the high magnification image group D1jn in the latest examination and the high magnification image group D1jf in the past examination. In this case, the alignment unit 131 acquires the fixation target position of each image from the storing unit 120. The alignment unit 131 refers to the relative positions from these fixation target positions in setting the initial search point in the alignment to be performed between the high magnification images D1jn in the latest examination and the wide viewing angle image D2n in the latest examination, to be performed between the wide viewing angle image D2n, and the wide viewing angle image D2f in the past examination, and to be performed between the wide viewing angle image D2f and the high magnification images D1jf in the past examination.

Any other conventional alignment method can be arbitrarily used. The alignment method used in the present exemplary embodiment includes a rough alignment according to which the alignment is performed using the Affine conversion method. A detailed alignment according to which the alignment is performed using the free form deformation (FFD) method (i.e., one of the nonrigid object alignment methods). The inter-image similarity used in any one of the above-mentioned alignments is a correlation coefficient, although any other conventionally known inter-image similarity can be used. Through the above-mentioned processing, pixels of the latest examination image (i.e., the wide viewing angle image D2n or the high magnification images D1jn) can be associated with pixels of the past examination image (i.e., the wide viewing angle image D2f or the high magnification images D1jf). The present invention is not limited to the alignment based on similarity between pixel values. For example, similar to the second exemplary embodiment, the ophthalmologic apparatus 10 can be configured to include the image feature acquiring unit 1321 in the individual image determination unit 132, so that the image feature acquiring unit 1321 can identify a capillary region and a feature-based alignment can be performed based on an identified blood vessel region.

<Step S560: Image Group Conformity Determination Processing>

The image group determination unit 133 determines the image group conformity based on the smallness of a non-observable (unanalyzable) region in comparison with regions having been imaged (or analyzed) in a different examination. If the image group conformity does not satisfy the predetermined criteria, the instructing unit 134 instructs the image acquiring unit 111 to perform the image re-capturing processing. In the present exemplary embodiment, the image group is composed of nine superimposing images as illustrated in FIG. 6G. An image number j is initially set on an upper-left image. The image number j increments successively according to the raster scanning (i.e., zigzag scanning) order. The following is a determination policy with respect to the conformity of the image composite (i.e., the image group), more specifically, the image group conformity required to observe the entire image composite under the same conditions.

1. The image composite does not include any image missing region (in other words, the luminance does not change discontinuously).
2. The image quality is stable irrespective of photographing position.

In this case, if the necessity of performing the image re-capturing processing is determined based on only the conformity of an individual image, instead of determining the image group conformity, strictly determining whether an imaging target region has been acquired will be necessary for each image. As a result, the image re-capturing will be frequently instructed. In this case, it will be necessary to set a wider overlapping region (i.e., increase the number of image pickup positions or widen the angle of view) to prevent the image re-capturing determination from increasing. Therefore, efficiently acquiring a high magnification image group satisfying the above-mentioned criteria 1 and 2 is feasible when the continuity or the subsidiarity of data in the edge portion or the overlapping region between neighboring images is taken into consideration in the conformity determination. Specifically, in the present exemplary embodiment, there is an overlapped region between two neighboring images (e.g., the gray region illustrated in FIG. 6F) or between four neighboring images (e.g., the black region illustrated in FIG. 6F). Even in a case where a single image includes an image missing region, if there is any data obtainable from the overlapped region between neighboring images, it is determined that the image group does not include any image missing region. Therefore, the image group conformity is determined according to the following procedure.

The procedure includes (1) forming a matrix-like composite composed of the individual images generated in step S540 according to the alignment parameter obtained in step S530.

The temporal image comparing unit 1331 checks the presence of any image missing region based on a comparison between the image composite generated in the above-mentioned process (1) and an image composite generated in the past examination.

Specifically, the temporal image comparing unit 1331 designates the composite of the image group D1jf of the past examination, i.e., a logical product ($\wedge(\vee_j D1jf)$) applied to a logical sum region ($\vee_j D1jf$) of the image group D1jf, as a temporal comparison target region. In the present exemplary embodiment, there are three image groups (of different examinations) to be subjected to the temporal comparison. Therefore, the temporal image comparing unit 1331 checks the presence of any image missing region in a case where the composite of the image group D1jf of each examination, i.e., a logical product $((\vee_j D1j1) \wedge (\vee_j D1j2) \wedge (\vee_j D1j3))$ applied to the logical sum region $\vee_j D1jf$, is designated as the temporal comparison target region. However, the comparison target region setting method is not limited to the above-mentioned example and any other arbitrary setting method can be used.

The procedure further includes (3) completing the formation of the image composite immediately if there is not any image missing region and (4) identifying the position of each image missing region if the image missing region is present and obtaining a number list of the image to which the image missing region belongs.

For example, according to the example illustrated in FIG. 6G, each of the high magnification image Dh6 and the high magnification image Dh9 includes an image missing region, as apparent from the comparison with the logical product region $(((\vee_j D1j1) \wedge (\vee_j D1j2) \wedge (\vee_j D1j3)))$ of the image composite in the past examination illustrated in FIG. 6H. Accordingly, the temporal image comparing unit 1331 obtains a number list (6 and 9) of the images including the image missing regions.

The procedure further includes (5) calculating the image group conformity according to the following formula.

$$\text{Formula:} \quad \text{(Total number of composite images} - \text{Number of images including any image missing region)} / \text{(Total number of composite images)}$$

The image group conformity is not limited to the above-mentioned example. Any other arbitrary index can be used if it is available to determine the image group conformity. For example, the image group conformity can be calculated according to the following formula.

$$\text{Formula:} \quad \text{(Area of the image composite generated in the process (1)} - \text{Area of the image missing region)} / \text{(Area of the image composite generated in the process (1))}$$

Further, in the present exemplary embodiment, the above-mentioned conditions 1 to 2 are referred to in determining the conformity of an image group (e.g., a still image group and a moving image group). However, the present invention is not limited to the above-mentioned example. For example, the image quality of an image composite can be referred to in determining the image group conformity. If the image quality of the latest examined image composite is equal to or greater than a lowest value of the image quality of the past examined image composite, the temporal image comparing unit 1331 can determine that the image quality of the latest examined image composite satisfies the image group conformity criteria.

<Step S570: Display>

The image processing unit 130 performs image group formation processing. The display control unit 135 causes the monitor 305 to display the formed image group (i.e., image composite).

Specifically, the image processing unit 130 performs the image group formation processing according to the following procedure.

The procedure further includes (6) acquiring a value ANmin that represents the number of superimposed frames that cooperatively constitute a superimposing image smallest in the number of superimposed frames, in the superimposing image group obtained through the individual image formation processing. In addition, the procedure includes setting the value ANmin as the number of images constituting the image composite and changing the number of frames to be superimposed at each photographing position to ANmin to generate a superimposing image. In this case, the image processing unit 130 starts, from the head of the frame group, selecting ANmin sheets of frames that can satisfy the criterion (a) relating to the luminance value in step S540 and generates a superimposing image based on the selected frames. The frame selection method is not limited to the above-mentioned example and any other arbitrary selection method is usable.

The procedure further includes (7) generating an image composite using the superimposing image generated in the above-mentioned process (6).

(FIG. 6H illustrates a result of the image re-capturing processing, which does not include any image missing region. The obtained image composite remains the same with respect to the number of superimposing images that cooperatively constitute the image composite.)

In the present exemplary embodiment, the high magnification image display by the monitor 305 is performed after completing the acquisition of all images. However, the present invention is not limited to the above-mentioned example. For example, after determining the conformity of each individual image, the display control unit 135 can cause the monitor 305 to display the determination result and/or a formed image, so that image capturing results can be sequentially confirmed. In this case, if there is an image that is determined as being low in conformity and requesting the image re-capturing processing, the display control unit 135 can cause the monitor 305 to perform an arbitrary discriminable display (e.g., giving color to a corresponding image pickup region or a frame thereof).

Further, in the present exemplary embodiment, the image composite to be formed based on the determination of the image group conformity is a composite of still images (i.e., superimposing images). However, the present invention is not limited to the above-mentioned example. For example, it is useful that data subsidiarity at an edge portion or an overlapping region between neighboring moving images is taken into consideration in determining the conformity and a moving image composite is displayed as illustrated in FIG. 6J.

Basic processing for displaying a composite of moving images is similar to that for displaying a composite of still images and different in the following point. More specifically, the image group formation processing includes (i) connecting the time-phase data acquiring apparatus 50 to the ophthalmologic apparatus 10 illustrated in FIG. 2B. The time-phase data acquiring apparatus 50 acquires time-phase data and a moving image beforehand and simultaneously. For example, the time-phase data is biological signal data acquired by a pulse wave detector. The cardiac cycle, more specifically, reproduction period, of each moving image can be obtained by referring to the time-phase data. In this case, the time-phase data acquiring apparatus 50 performs frame interpolation processing on moving images to eliminate any difference in the reproduction period between the moving images (i.e., between the photographing positions and/or between the examinations).

The image group formation processing further includes (ii) selecting the longest consecutive frame section that does not include any luminance abnormal frame in the image formation processing for each photographing position.

The image group formation processing further includes (iii) performing conformity determination processing according to the following policy in the image group conformity determination processing.

1. The image composite does not include any image missing region.
2. The number of reproduction frames (pulsation cycle) is substantially the same at each photographing position.
3. The number of reproduction frames (pulsation cycle) is substantially the same in each examination.

(iv) The frames selected in the above-mentioned process (6) of the image group formation processing are frames in a consecutive frame section.

Through the above-mentioned processing, it becomes feasible to eliminate any image missing region in the display of a composite of moving images. Further, it becomes feasible to form a moving image composite composed of consecutive frames that are identical in the number of reproduction frames. Further, in a case where no time-phase data has been acquired, it is feasible to display a composite of moving images without adjusting the reproduction time.

According to the above-mentioned configuration, the ophthalmologic apparatus 10 determines the image group conformity based on the smallness of a non-observable (unanalyzable) region in comparison with regions having been imaged (or analyzed) in a different examination in displaying a composite of high-magnification adaptive optics SLO images captured at different photographing positions. Through the above-mentioned processing, in a case where an observation or analysis target cell group (or tissue) and a lesion thereof extend beyond the acquisition positions of a plurality of high magnification images, it becomes feasible to capture a group of observable or analyzable images under substantially the same conditions.

Other Exemplary Embodiment

In the above-mentioned exemplary embodiment, the ophthalmologic apparatus 10 gives automatically an instruction on the necessity of performing the image re-capturing processing and the image capturing conditions for the next image based on the image group conformity. However, the present invention is not limited to the above-mentioned exemplary embodiment.

For example, the ophthalmologic apparatus 10 can be configured to enable a user to designate an image that requires image re-capturing processing via the instruction acquiring unit 140. In this case, the image re-capturing necessity instructing unit 1341 instructs the image acquiring unit 111 to perform the image re-capturing processing. Further, for example, the ophthalmologic apparatus 10 can be configured to enable a user to designate the position of a next imaging target image via the instruction acquiring unit 140. In this case, the image capturing condition instructing unit 1342 instructs the image acquiring unit 111 to set photographing conditions for the next image. In this case, the display control unit 135 can cause the monitor 305 to put a discriminable mark (e.g. a color frame) to the image that requires the image re-capturing processing. Further, in a case where there is a specific photographing position at which data cannot be acquired due to examinee's eye characteristics (e.g., clouding of an intermediate light transmission body), it is useful that a user can manually designate an image re-capturing position or an image non-capturing position so that the designated position can be excluded in the image group conformity determination processing or the image re-capturing necessity determination processing, or can be prevented from being designated as the next image photographing condition setting target.

The above-mentioned exemplary embodiment is characterized by determining the conformity based on a single image group. However, the exemplary embodiment of the present invention is not limited to the above-mentioned example. For example, in a case where a single examination includes acquiring a plurality of image groups as illustrated in FIGS. 15A and 15B, the ophthalmologic apparatus 10 can determine the image group conformity for each image group and give an instruction on the necessity of image re-capturing processing or give an instruction on image capturing conditions for the next image, similar to the above-mentioned exemplary embodiment. Subsequently, the ophthalmologic apparatus 10 can determine the conformity between the image groups and can give an instruction on the necessity of image re-capturing processing or give an instruction on image capturing conditions for the next image based on the conformity between the image groups.

FIG. 15A illustrates a low-magnification image composite composed of adaptive optics SLO images and a high-magnification image composite composed of adaptive optics SLO images. In this case, first, the ophthalmologic apparatus 10 determines the image group conformity for each of the low-magnification image composite and the high-magnification image composite. Then, the ophthalmologic apparatus 10 gives an instruction on the necessity of performing image re-capturing processing for each image composite. Further, the ophthalmologic apparatus 10 determines the conformity between different magnifications (e.g., Area of a logical sum region of the high magnification image D1j group that does not protrude from the image pickup region of the low magnification image D2k group)/(Area of the logical sum region of the entire high magnification image D1j group). Then, the ophthalmologic apparatus 10 gives an instruction on the necessity of performing the image re-capturing processing based on the determined conformity.

FIG. 15B illustrates a multi-configuration type image composite composed of a plurality of image groups MnDhj. In this case, similar to the above-mentioned exemplary embodiment, the ophthalmologic apparatus 10 first determines the conformity of each image group and then gives an instruction on the necessity of image re-capturing processing or image capturing conditions for the next image. Then, the ophthalmologic apparatus 10 determines the conformity between the image groups (e.g., the conformity between neighboring image groups) and gives an instruction on the necessity of image re-capturing processing or image capturing conditions for the next image based on the determined conformity between the image groups. For example, the conformity between the image groups can be defined referring to the similarity between image groups with respect to average luminance or S/N ratio. Further, in constituting the multi-configuration type image composite, it is acceptable to determine the distance between neighboring image groups arbitrarily, even when any overlapping region is formed between neighboring image groups. Further, it is acceptable to determine the size of each image group (e.g., the acquisition position number of the images that constitute an image group) arbitrarily.

Figure 15C:
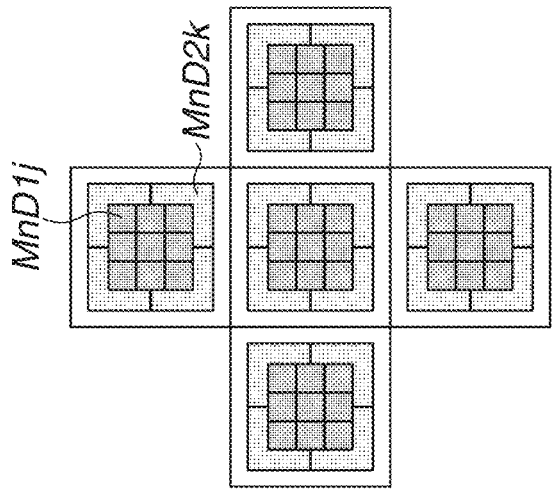
FIGS. 15A, 15B, and 15C illustrate the contents of image processing according to another exemplary embodiment of the present invention.
Figure 15B:
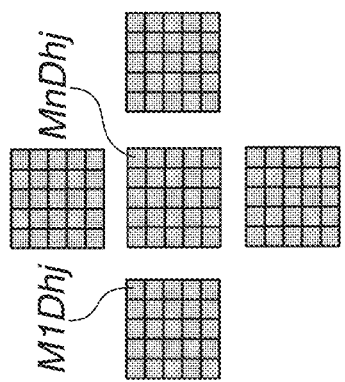
Figure 15A:
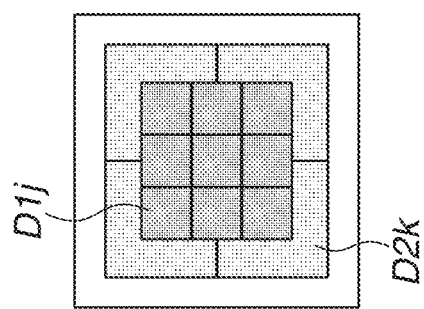

FIG. 15C illustrates another multi-configuration type image composite including a plurality of image groups that are different in magnification. According the illustrated example, the present invention is applicable in any case although the ophthalmologic apparatus 10 may prioritize the determination of the conformity between the different magnification image groups or prioritize the conformity between the image groups at the different acquisition positions.

Further, the alignment target images include SLO images or tomographic images of an eye, in the above-mentioned exemplary embodiments. However, the present invention is not limited to the above-mentioned examples. For example, the wide viewing angle image Dl can be a fundus camera image and the high magnification images Dh can be adaptive optics fundus camera images. Further, appropriately combining images that are different in modality is feasible. For example, when the wide viewing angle image Dl is a wide viewing angle SLO image, the high magnification images Dh can be projection images of adaptive optics tomographic images. Further, when the wide viewing angle image Dl is an adaptive optics tomographic image, the high magnification image images Dh can be adaptive optics SLO images. Further, the adaptive optics SLO image capturing apparatus 20 and the tomographic image capturing apparatus 60 can be integrated with a multi-function peripheral and can be directly connected to the ophthalmologic apparatus 10.

Further, as described in the above-mentioned exemplary embodiments, the present invention can be realized as an ophthalmologic apparatus. However, the present invention is not limited to the ophthalmologic apparatus. For example, the present invention encompasses a software program that can be executed by a CPU of a computer. Further, the present invention encompasses a storage medium that stores the above-mentioned software program.

In this case, in determining photographing conditions, it is desired to use at least one of the edge portion and the overlapping region of a plurality of images. It is desired that the ophthalmologic apparatus includes a comparing unit (e.g., the image group determination unit 133 illustrated in FIG. 1) configured to compare an image composite with a wide viewing angle image that has a wider angle of view in comparison with respective images constituting the image composite. In this case, the determination unit can determine a value indicating the continuity based on a comparison result obtained by the comparing unit. Further, it is desired that the ophthalmologic apparatus includes a display control unit (e.g., the display control unit 135 illustrated in FIG. 1) configured to cause the display unit to display an image composite composed of a plurality of images captured at different positions of an eye based on determined photographing conditions and/or display the determined photographing conditions. Further, it is desired to extract a blood vessel from an image composite automatically (or semi-automatically or in response to a manual instruction) and measure the moving speed of a blood corpuscle in the extracted blood vessel. Further, as another example, the display control unit can cause the display unit to display a plurality of images side by side or selectively display each of the images.

Other Exemplary Embodiment

The present invention can be realized by performing the following processing. More specifically, the processing includes supplying a software program that can realize the functions of the above-mentioned exemplary embodiments, to a system or an apparatus via a network or an appropriate storage medium, and causing a computer (or a CPU or a MPU) of the system or the apparatus to read and execute the program.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-181341, filed Sep. 5, 2014, which is hereby incorporated by reference herein in its entirety.

What is claimed is:

1. A method for controlling an ophthalmologic apparatus that acquires a plurality of images by photographing a plurality of different regions of an eye at different times to generate one image by using the acquired plurality of images, the plurality of different regions being set in a region to be photographed of the eye, the method comprising:
   determining a image group conformity from the plurality of images of the plurality of different regions;
   determining, based on the determined image group conformity, at least one image missing region; and
   controlling an ophthalmologic apparatus in such a way as to re-photograph the determined at least one image missing region.

2. An ophthalmologic apparatus that acquires a plurality of images by photographing a plurality of different regions of an eye at different times to generate one image by using the acquired plurality of images, the plurality of different regions being set in a region to be photographed of the eye, the ophthalmologic apparatus comprising:
   at least one memory that stores a program of instructions; and
   at least one processor, coupled to the at least one memory, that executes the program of instructions to cause the ophthalmologic apparatus to implement:
   determining an image group conformity from the plurality of images of the plurality of different regions;
   determining, based on the determined image group conformity, at least one image missing region within the region to be photographed; and
   controlling the ophthalmologic apparatus in such a way as to re-photograph the determined at least one image missing region.

3. The ophthalmologic apparatus according to claim 2, further comprising a scanning optical system that is configured to scan the eye with measurement light,
   wherein the controlling controls the scanning optical system in such a way as to scan the determined at least one image missing region with the measurement light.

4. The ophthalmologic apparatus according to claim 2, further comprising a scanning optical system that is configured to scan the eye with measurement light,
   wherein the controlling controls a position of a fixation target being set to fixate the eye in such a way as to scan the determined at least one image missing region with the measurement light.

5. The ophthalmologic apparatus according to claim 2, further comprising a wavefront correcting device configured to correct a wavefront of at least one of measurement light and return light from the eye being irradiated with the measurement light,
   wherein the ophthalmologic apparatus uses the wavefront corrected light in acquiring the plurality of images.

6. The ophthalmologic apparatus according to claim 2, wherein the at least one processor executes the program of instructions to further cause the ophthalmologic apparatus to display the generated one image including the plurality of images photographed at different positions of the eye.

7. The ophthalmologic apparatus according to claim 2, wherein the at least one processor executes the program of instructions to further cause the ophthalmologic apparatus to display information about the determined at least one image missing region.

8. The ophthalmologic apparatus according to claim 2, wherein the at least one image missing region is, after sequentially photographing the plurality of different regions, determined by analyzing the plurality of images, the plurality of images being acquired by sequentially photographing the plurality of different regions.

9. The ophthalmologic apparatus according to claim 2, wherein the least one processor executes the program of instructions to cause the ophthalmologic apparatus to implement: generating one image by using the plurality of images and the re-photographed at least one image missing region, the plurality of images being acquired by sequentially photographing the plurality of different regions.

10. The ophthalmologic apparatus according to claim 2, wherein a part of the plurality of different regions is overlapped, and determines, based on the determined image group conformity, the at least one image missing region using information indicating image discontinuity between the acquired plurality of images relative to a prospective image missing region.

11. The ophthalmologic apparatus according to claim 10, wherein the determining determines the at least one image missing region using information indicating the characteristic continuity between the plurality of images with respect to at least one of a relative position, luminance characteristics, and image features.

12. The ophthalmologic apparatus according to claim 10, wherein the determining determines the at least one image missing region using information indicating the characteristic continuity between the plurality of images, in at least one of an edge portion and an overlapping region of the plurality of images.

13. The ophthalmologic apparatus according to claim 10, wherein the determining determines the at least one image missing region using information about the generated one image, as the information indicating the characteristic continuity.

14. The ophthalmologic apparatus according to claim 10, wherein the determining determines the at least one image missing region using information about at least one of total number, area, and non-blood vessel region boundary length of the images that constitute the generated one image, as the information indicating the characteristic continuity.

15. The ophthalmologic apparatus according to claim 10, wherein the at least one processor executes the program of instructions to further cause the ophthalmologic apparatus to compare the generated one image with a wide viewing angle image having an angle of view wider than that of each of the acquired plurality of images,
wherein the determining determines the at least one image missing region using information about a comparison result obtained by such comparing.

16. The ophthalmologic apparatus according to claim 2, wherein the determining determines the at least one image missing region using information about image group conformity of the acquired plurality of images.

17. The ophthalmologic apparatus according to claim 16, wherein the determining determines the at least one image missing region using information about at least one of a relative position, continuity in luminance characteristics, and similarity in image quality between images in the same examination, and image features of the acquired plurality of images, as information about the image group conformity.

18. The ophthalmologic apparatus according to claim 16, wherein the determining determines the at least one image missing region using information about at least one of a relative position, continuity in luminance characteristics, and similarity in image quality between image groups in different examinations, as information about the image group conformity.

19. The ophthalmologic apparatus according to claim 16, wherein the at least one processor executes the program of instructions to further cause the ophthalmologic apparatus to display the generated one image including images acquired based on the instructed photographing conditions.

20. The ophthalmologic apparatus according to claim 16, wherein the at least one processor executes the program of instructions to further cause the ophthalmologic apparatus to measure a moving speed of a blood corpuscle in the image acquired based on the instructed photographing conditions.

* * * * *